(12) United States Patent
Deen et al.

(10) Patent No.: US 12,109,137 B2
(45) Date of Patent: Oct. 8, 2024

(54) MEDICAL DEVICE DELIVERY

(71) Applicant: Covidien LP, Mansfield, MA (US)

(72) Inventors: Daniel Deen, Long Beach, CA (US); Ashok Nageswaran, Irvine, CA (US)

(73) Assignee: COVIDIEN LP, Mansfield, MA (US)

( * ) Notice: Subject to any disclaimer, the term of this patent is extended or adjusted under 35 U.S.C. 154(b) by 207 days.

(21) Appl. No.: 17/444,149

(22) Filed: Jul. 30, 2021

(65) Prior Publication Data

US 2023/0029736 A1  Feb. 2, 2023

(51) Int. Cl.
*A61F 2/966* (2013.01)
*A61F 2/95* (2013.01)

(52) U.S. Cl.
CPC ............ *A61F 2/966* (2013.01); *A61F 2/9526* (2020.05); *A61F 2210/0014* (2013.01)

(58) Field of Classification Search
CPC .......... A61F 2/966; A61F 2/958; A61F 2/962; A61F 2002/9665; A61F 2/243; A61F 2/95–2/97; A61B 2017/00867
See application file for complete search history.

(56) References Cited

U.S. PATENT DOCUMENTS

| | | |
|---|---|---|
| 3,416,531 A | 12/1968 | Lowell |
| 4,364,391 A | 12/1982 | Toye |
| 4,425,919 A | 1/1984 | Alston et al. |
| 4,516,972 A | 5/1985 | Samson |
| 4,723,936 A | 2/1988 | Buchbinder et al. |
| 4,877,031 A | 10/1989 | Conway et al. |
| 4,990,151 A | 2/1991 | Wallsten |
| 5,011,478 A | 4/1991 | Cope |
| 5,026,377 A | 6/1991 | Burton et al. |
| 5,037,404 A | 8/1991 | Gold et al. |
| 5,037,427 A * | 8/1991 | Harada ............... A61F 2/95 606/108 |
| 5,061,275 A | 10/1991 | Wallsten et al. |
| 5,098,393 A | 3/1992 | Amplatz et al. |

(Continued)

FOREIGN PATENT DOCUMENTS

| | | |
|---|---|---|
| CN | 104582643 A | 4/2015 |
| CN | 105232195 A | 1/2016 |

(Continued)

OTHER PUBLICATIONS

Dieter Stoeckel, et al., Self-expanding nitinol stents: material and design considerations, Sep. 3, 2003, Springer-Verlag, pp. 292-301. (Year: 2003).*

(Continued)

*Primary Examiner* — Kathleen S Holwerda
*Assistant Examiner* — Daniel Icet
(74) *Attorney, Agent, or Firm* — Fortem IP LLP

(57) ABSTRACT

A stent delivery system includes a core member and an expandable member coupled to the core member distal segment. A stent extends along the core member distal segment such that an inner surface of the stent is positioned over the expandable member. The stent has a primary heat-set configuration where the stent is radially expanded, and a secondary heat-set configuration where the stent is radially compressed. The expandable member is adapted to radially expand at least a portion of the stent from a radially compressed configuration toward a radially expanded configuration.

19 Claims, 8 Drawing Sheets

(56) References Cited

U.S. PATENT DOCUMENTS

| | | |
|---|---|---|
| 5,108,411 A | 4/1992 | Mckenzie |
| 5,147,370 A | 9/1992 | Mcnamara et al. |
| 5,178,158 A | 1/1993 | De |
| 5,201,316 A | 4/1993 | Pomeranz et al. |
| 5,209,734 A | 5/1993 | Hurley et al. |
| 5,279,562 A | 1/1994 | Sirhan et al. |
| 5,279,596 A | 1/1994 | Castaneda et al. |
| 5,292,311 A | 3/1994 | Cope |
| 5,318,032 A | 6/1994 | Lonsbury et al. |
| 5,318,525 A | 6/1994 | West et al. |
| 5,318,529 A | 6/1994 | Kontos |
| 5,358,493 A | 10/1994 | Schweich et al. |
| 5,382,259 A | 1/1995 | Phelps et al. |
| 5,389,087 A | 2/1995 | Miraki |
| 5,403,292 A | 4/1995 | Ju |
| 5,437,288 A | 8/1995 | Schwartz et al. |
| 5,445,646 A | 8/1995 | Euteneuer et al. |
| 5,454,795 A | 10/1995 | Samson |
| 5,458,605 A | 10/1995 | Klemm |
| 5,474,563 A | 12/1995 | Myler et al. |
| 5,478,349 A | 12/1995 | Nicholas |
| 5,484,444 A | 1/1996 | Braunschweiler et al. |
| 5,496,294 A | 3/1996 | Hergenrother et al. |
| 5,499,975 A | 3/1996 | Cope et al. |
| 5,522,822 A | 6/1996 | Phelps et al. |
| 5,531,721 A | 7/1996 | Pepin et al. |
| 5,534,007 A | 7/1996 | St et al. |
| 5,545,209 A | 8/1996 | Roberts et al. |
| 5,554,139 A | 9/1996 | Okajima |
| 5,569,220 A | 10/1996 | Webster |
| 5,571,135 A | 11/1996 | Fraser et al. |
| 5,573,520 A | 11/1996 | Schwartz et al. |
| 5,584,821 A | 12/1996 | Hobbs et al. |
| 5,599,325 A | 2/1997 | Ju et al. |
| 5,599,326 A | 2/1997 | Carter |
| 5,601,539 A | 2/1997 | Corso |
| 5,636,641 A | 6/1997 | Fariabi |
| 5,645,559 A | 7/1997 | Hachtman et al. |
| 5,658,264 A | 8/1997 | Samson |
| 5,662,622 A | 9/1997 | Gore et al. |
| 5,676,659 A | 10/1997 | Mcgurk |
| 5,695,483 A | 12/1997 | Samson |
| 5,695,499 A | 12/1997 | Helgerson et al. |
| 5,702,373 A | 12/1997 | Samson |
| 5,702,418 A | 12/1997 | Ravenscroft |
| 5,704,926 A | 1/1998 | Sutton |
| 5,709,703 A | 1/1998 | Lukic et al. |
| 5,711,909 A | 1/1998 | Gore et al. |
| 5,716,410 A * | 2/1998 | Wang ............... A61M 25/1027 623/1.22 |
| 5,725,513 A | 3/1998 | Ju et al. |
| 5,725,571 A | 3/1998 | Imbert et al. |
| 5,728,063 A | 3/1998 | Preissman et al. |
| 5,741,429 A | 4/1998 | Donadio et al. |
| 5,743,876 A | 4/1998 | Swanson |
| 5,755,777 A | 5/1998 | Chuter |
| 5,759,173 A | 6/1998 | Preissman et al. |
| 5,776,141 A | 7/1998 | Klein et al. |
| 5,782,811 A | 7/1998 | Samson et al. |
| 5,791,036 A | 8/1998 | Goodin et al. |
| 5,824,041 A | 10/1998 | Lenker et al. |
| 5,833,632 A | 11/1998 | Jacobsen et al. |
| 5,836,925 A | 11/1998 | Soltesz |
| 5,836,926 A | 11/1998 | Peterson et al. |
| 5,851,203 A | 12/1998 | Van |
| 5,853,400 A | 12/1998 | Samson |
| 5,873,866 A | 2/1999 | Kondo et al. |
| 5,876,386 A | 3/1999 | Samson |
| 5,891,112 A | 4/1999 | Samson |
| 5,897,529 A | 4/1999 | Ponzi |
| 5,897,537 A | 4/1999 | Berg et al. |
| 5,902,290 A | 5/1999 | Peacock et al. |
| 5,906,605 A | 5/1999 | Coxum |
| 5,935,161 A | 8/1999 | Robinson et al. |
| 5,938,653 A | 8/1999 | Pepin |
| 5,951,494 A | 9/1999 | Wang et al. |
| 5,951,539 A | 9/1999 | Nita et al. |
| 5,961,510 A | 10/1999 | Fugoso et al. |
| 5,968,053 A | 10/1999 | Revelas |
| 5,968,069 A | 10/1999 | Dusbabek et al. |
| 5,971,975 A | 10/1999 | Mills et al. |
| 5,984,963 A | 11/1999 | Ryan et al. |
| 6,017,323 A | 1/2000 | Chee |
| 6,030,371 A | 2/2000 | Pursley |
| 6,045,547 A | 4/2000 | Ren et al. |
| 6,053,903 A | 4/2000 | Samson |
| 6,053,904 A | 4/2000 | Scribner et al. |
| 6,077,258 A | 6/2000 | Lange et al. |
| 6,077,295 A | 6/2000 | Limon et al. |
| 6,077,297 A | 6/2000 | Robinson et al. |
| 6,083,152 A | 7/2000 | Strong |
| 6,093,177 A | 7/2000 | Javier et al. |
| 6,105,651 A | 8/2000 | Leanna |
| 6,106,510 A | 8/2000 | Lunn et al. |
| 6,106,540 A | 8/2000 | Dehdashtian et al. |
| 6,123,723 A | 9/2000 | Konya et al. |
| 6,126,685 A | 10/2000 | Lenker et al. |
| 6,135,992 A | 10/2000 | Wang |
| 6,149,680 A | 11/2000 | Shelso et al. |
| 6,152,912 A | 11/2000 | Jansen et al. |
| 6,152,944 A | 11/2000 | Holman et al. |
| 6,159,219 A | 12/2000 | Ren |
| 6,165,163 A | 12/2000 | Chien et al. |
| 6,165,166 A | 12/2000 | Samuelson et al. |
| 6,171,295 B1 | 1/2001 | Garabedian et al. |
| 6,171,296 B1 | 1/2001 | Chow |
| 6,171,297 B1 | 1/2001 | Pedersen et al. |
| 6,186,986 B1 | 2/2001 | Berg et al. |
| 6,193,739 B1 | 2/2001 | Chevillon et al. |
| 6,197,015 B1 | 3/2001 | Wilson |
| 6,217,565 B1 | 4/2001 | Cohen |
| 6,217,566 B1 | 4/2001 | Ju et al. |
| 6,251,132 B1 | 6/2001 | Ravenscroft et al. |
| 6,258,080 B1 | 7/2001 | Samson |
| 6,264,683 B1 | 7/2001 | Stack et al. |
| 6,287,315 B1 | 9/2001 | Wijeratne et al. |
| 6,325,807 B1 | 12/2001 | Que |
| 6,350,278 B1 | 2/2002 | Lenker et al. |
| 6,355,027 B1 | 3/2002 | Le et al. |
| 6,358,238 B1 | 3/2002 | Sherry |
| 6,358,460 B1 | 3/2002 | Hunt et al. |
| 6,368,316 B1 | 4/2002 | Jansen et al. |
| 6,371,953 B1 | 4/2002 | Beyar et al. |
| 6,383,171 B1 | 5/2002 | Gifford et al. |
| 6,387,118 B1 | 5/2002 | Hanson |
| 6,389,087 B1 | 5/2002 | Heinonen et al. |
| 6,395,008 B1 | 5/2002 | Ellis et al. |
| 6,395,017 B1 | 5/2002 | Dwyer et al. |
| 6,398,791 B1 | 6/2002 | Que et al. |
| 6,419,693 B1 | 7/2002 | Fariabi |
| 6,425,898 B1 | 7/2002 | Wilson et al. |
| 6,428,552 B1 | 8/2002 | Sparks |
| 6,443,971 B1 | 9/2002 | Boylan et al. |
| 6,458,075 B1 | 10/2002 | Sugiyama et al. |
| 6,464,684 B1 | 10/2002 | Galdonik |
| 6,468,298 B1 | 10/2002 | Pelton |
| 6,475,184 B1 | 11/2002 | Wang et al. |
| 6,494,907 B1 | 12/2002 | Bulver |
| 6,508,804 B2 | 1/2003 | Sarge et al. |
| 6,508,805 B1 | 1/2003 | Garabedian et al. |
| 6,508,806 B1 | 1/2003 | Hoste |
| 6,517,547 B1 | 2/2003 | Feeser et al. |
| 6,554,820 B1 | 4/2003 | Wendlandt et al. |
| 6,562,021 B1 | 5/2003 | Derbin et al. |
| 6,562,063 B1 | 5/2003 | Euteneuer et al. |
| 6,576,006 B2 | 6/2003 | Limon et al. |
| 6,582,460 B1 | 6/2003 | Cryer |
| 6,589,227 B2 | 7/2003 | Soenderskov |
| 6,602,271 B2 | 8/2003 | Adams et al. |
| 6,607,551 B1 | 8/2003 | Sullivan et al. |
| 6,622,367 B1 | 9/2003 | Bolduc et al. |
| 6,635,047 B2 | 10/2003 | Forsberg |
| 6,638,245 B2 | 10/2003 | Miller et al. |
| 6,641,564 B1 | 11/2003 | Kraus |

(56) References Cited

U.S. PATENT DOCUMENTS

| | | |
|---|---|---|
| 6,648,654 B1 | 11/2003 | Hembree |
| 6,648,874 B2 | 11/2003 | Parisi et al. |
| 6,652,508 B2 | 11/2003 | Griffin et al. |
| 6,663,614 B1 | 12/2003 | Carter |
| 6,669,719 B2 | 12/2003 | Wallace et al. |
| 6,689,120 B1 | 2/2004 | Gerdts |
| 6,699,274 B2 | 3/2004 | Stinson |
| 6,702,782 B2 | 3/2004 | Miller et al. |
| 6,706,055 B2 | 3/2004 | Douk et al. |
| 6,716,207 B2 | 4/2004 | Farnholtz |
| 6,726,659 B1 | 4/2004 | Stocking et al. |
| 6,764,504 B2 | 7/2004 | Wang et al. |
| 6,808,529 B2 | 10/2004 | Fulkerson |
| 6,814,749 B2 | 11/2004 | Cox et al. |
| 6,815,325 B2 | 11/2004 | Ishii |
| 6,817,995 B1 | 11/2004 | Halpern |
| 6,830,575 B2 | 12/2004 | Stenzel et al. |
| 6,837,890 B1 | 1/2005 | Chludzinski et al. |
| 6,843,802 B1 | 1/2005 | Villalobos et al. |
| 6,858,024 B1 | 2/2005 | Berg et al. |
| 6,866,660 B2 | 3/2005 | Garabedian et al. |
| 6,866,679 B2 | 3/2005 | Kusleika |
| 6,932,837 B2 | 8/2005 | Amplatz et al. |
| 6,939,353 B2 | 9/2005 | Que et al. |
| 6,945,970 B2 | 9/2005 | Pepin |
| 6,960,227 B2 | 11/2005 | Jones et al. |
| 6,984,963 B2 | 1/2006 | Pidutti et al. |
| 6,989,024 B2 | 1/2006 | Hebert et al. |
| 7,001,369 B2 | 2/2006 | Griffin et al. |
| 7,011,675 B2 | 3/2006 | Hemerick et al. |
| 7,025,758 B2 | 4/2006 | Klint |
| 7,074,236 B2 | 7/2006 | Rabkin et al. |
| 7,104,979 B2 | 9/2006 | Jansen et al. |
| 7,147,656 B2 | 12/2006 | Andreas et al. |
| 7,156,860 B2 | 1/2007 | Wallsten |
| 7,163,523 B2 | 1/2007 | Devens et al. |
| 7,166,088 B2 | 1/2007 | Heuser |
| 7,166,099 B2 | 1/2007 | Devens |
| 7,166,100 B2 | 1/2007 | Jordan et al. |
| 7,172,575 B2 | 2/2007 | El-Nounou et al. |
| 7,223,263 B1 | 5/2007 | Seno |
| 7,228,878 B2 | 6/2007 | Chen et al. |
| 7,306,624 B2 | 12/2007 | Yodfat et al. |
| 7,323,000 B2 | 1/2008 | Monstdt et al. |
| 7,331,948 B2 | 2/2008 | Skarda |
| 7,357,812 B2 | 4/2008 | Andreas et al. |
| 7,371,248 B2 | 5/2008 | Dapolito et al. |
| 7,402,151 B2 | 7/2008 | Rosenman et al. |
| 7,404,820 B2 | 7/2008 | Mazzocchi et al. |
| 7,427,288 B2 | 9/2008 | Sater |
| 7,438,712 B2 | 10/2008 | Chouinard |
| 7,445,684 B2 | 11/2008 | Pursley |
| 7,473,271 B2 | 1/2009 | Gunderson |
| 7,473,272 B2 | 1/2009 | Pryor |
| 7,481,804 B2 | 1/2009 | Devens |
| 7,507,229 B2 | 3/2009 | Hewitt et al. |
| 7,524,322 B2 | 4/2009 | Monstadt et al. |
| 7,556,634 B2 | 7/2009 | Lee et al. |
| 7,556,710 B2 | 7/2009 | Leeflang et al. |
| 7,569,046 B2 | 8/2009 | Zhou |
| 7,572,290 B2 | 8/2009 | Yodfat et al. |
| 7,582,079 B2 | 9/2009 | Wendlandt et al. |
| 7,597,830 B2 | 10/2009 | Zhou |
| 7,621,904 B2 | 11/2009 | Mcferran et al. |
| 7,641,646 B2 | 1/2010 | Kennedy |
| 7,651,520 B2 | 1/2010 | Fischell et al. |
| 7,655,031 B2 | 2/2010 | Tenne et al. |
| 7,674,411 B2 | 3/2010 | Berg et al. |
| 7,691,138 B2 | 4/2010 | Stenzel et al. |
| 7,708,704 B2 | 5/2010 | Mitelberg et al. |
| 7,717,953 B2 | 5/2010 | Kaplan et al. |
| 7,740,652 B2 | 6/2010 | Gerdts et al. |
| 7,758,624 B2 | 7/2010 | Dorn et al. |
| 7,766,820 B2 | 8/2010 | Core |
| 7,766,896 B2 | 8/2010 | Kornkven et al. |
| 7,780,646 B2 | 8/2010 | Farnholtz |
| 7,815,600 B2 | 10/2010 | Al-Marashi et al. |
| 7,815,608 B2 | 10/2010 | Schafersman et al. |
| 7,815,628 B2 | 10/2010 | Devens |
| 7,828,790 B2 | 11/2010 | Griffin |
| 7,867,267 B2 | 1/2011 | Sullivan et al. |
| 7,879,022 B2 | 2/2011 | Bonnette et al. |
| 7,935,140 B2 | 5/2011 | Griffin |
| 7,942,925 B2 | 5/2011 | Yodfat et al. |
| 7,955,370 B2 | 6/2011 | Gunderson |
| 7,981,148 B2 | 7/2011 | Aguilar et al. |
| 7,993,385 B2 | 8/2011 | Levine et al. |
| 8,025,692 B2 | 9/2011 | Feeser |
| 8,034,095 B2 | 10/2011 | Randolph et al. |
| 8,042,720 B2 | 10/2011 | Shifrin et al. |
| 8,048,104 B2 | 11/2011 | Monstadt et al. |
| 8,066,754 B2 | 11/2011 | Malewicz |
| 8,083,791 B2 | 12/2011 | Kaplan et al. |
| 8,088,140 B2 | 1/2012 | Ferrera et al. |
| 8,092,508 B2 | 1/2012 | Leynov et al. |
| 8,109,987 B2 | 2/2012 | Kaplan et al. |
| 8,133,266 B2 | 3/2012 | Thomas et al. |
| 8,147,534 B2 | 4/2012 | Berez et al. |
| 8,187,314 B2 | 5/2012 | Davis et al. |
| 8,257,432 B2 | 9/2012 | Kaplan et al. |
| 8,298,276 B2 | 10/2012 | Ozawa et al. |
| 8,317,850 B2 | 11/2012 | Kusleika |
| 8,337,543 B2 | 12/2012 | Jordan et al. |
| 8,366,763 B2 | 2/2013 | Davis et al. |
| 8,382,818 B2 | 2/2013 | Davis et al. |
| 8,480,701 B2 | 7/2013 | Monstadt |
| 8,579,958 B2 | 11/2013 | Kusleika |
| 8,591,566 B2 | 11/2013 | Newell et al. |
| 8,597,321 B2 | 12/2013 | Monstadt et al. |
| 8,636,760 B2 | 1/2014 | Garcia et al. |
| 8,679,172 B2 | 3/2014 | Dorn et al. |
| 8,790,387 B2 | 7/2014 | Nguyen et al. |
| 8,858,613 B2 | 10/2014 | Cragg et al. |
| 8,968,383 B1 | 3/2015 | Johnson et al. |
| 9,241,782 B2 * | 1/2016 | Besselink ............... A61F 2/91 |
| 9,393,141 B2 | 7/2016 | Gerdts et al. |
| 9,433,520 B2 * | 9/2016 | Longo ................. A61F 2/966 |
| 9,439,795 B2 | 9/2016 | Wang et al. |
| 9,474,639 B2 | 10/2016 | Haggstrom et al. |
| 9,775,733 B2 | 10/2017 | Johnson et al. |
| 9,782,186 B2 | 10/2017 | Johnson et al. |
| 9,827,126 B2 | 11/2017 | Losordo et al. |
| 10,786,377 B2 | 9/2020 | Nageswaran et al. |
| 10,945,867 B2 | 3/2021 | Nageswaran et al. |
| 11,071,637 B2 | 7/2021 | Dawson et al. |
| 11,944,558 B2 | 4/2024 | Deen et al. |
| 2001/0020173 A1 | 9/2001 | Klumb et al. |
| 2001/0027310 A1 | 10/2001 | Parisi et al. |
| 2001/0029362 A1 | 10/2001 | Sirhan et al. |
| 2001/0044591 A1 | 11/2001 | Stevens et al. |
| 2001/0049547 A1 | 12/2001 | Moore |
| 2002/0029046 A1 | 3/2002 | Lorentzen et al. |
| 2002/0045929 A1 | 4/2002 | Diaz |
| 2002/0049412 A1 | 4/2002 | Madrid et al. |
| 2002/0072789 A1 | 6/2002 | Hackett et al. |
| 2002/0107526 A1 | 8/2002 | Greenberg et al. |
| 2002/0111666 A1 | 8/2002 | Hart et al. |
| 2002/0138128 A1 | 9/2002 | Stiger et al. |
| 2002/0156459 A1 | 10/2002 | Ye et al. |
| 2002/0156460 A1 | 10/2002 | Ye et al. |
| 2002/0165523 A1 | 11/2002 | Chin et al. |
| 2002/0188342 A1 | 12/2002 | Rykhus et al. |
| 2003/0004539 A1 | 1/2003 | Linder et al. |
| 2003/0009208 A1 | 1/2003 | Snyder et al. |
| 2003/0050600 A1 | 3/2003 | Ressemann et al. |
| 2003/0191451 A1 | 10/2003 | Gilmartin |
| 2003/0212410 A1 | 11/2003 | Stenzel et al. |
| 2003/0212430 A1 | 11/2003 | Bose et al. |
| 2004/0024416 A1 | 2/2004 | Yodfat et al. |
| 2004/0092868 A1 | 5/2004 | Murray |
| 2004/0092879 A1 | 5/2004 | Kraus et al. |
| 2004/0111095 A1 | 6/2004 | Gordon et al. |
| 2004/0143239 A1 | 7/2004 | Zhou et al. |
| 2004/0147903 A1 | 7/2004 | Latini |

(56) References Cited

U.S. PATENT DOCUMENTS

| | | |
|---|---|---|
| 2004/0158230 A1 | 8/2004 | Hunn et al. |
| 2004/0181174 A2 | 9/2004 | Davis et al. |
| 2004/0193140 A1 | 9/2004 | Griffin et al. |
| 2004/0193243 A1 | 9/2004 | Mangiardi et al. |
| 2004/0204749 A1 | 10/2004 | Gunderson |
| 2004/0220585 A1 | 11/2004 | Nikolchev et al. |
| 2004/0230285 A1 | 11/2004 | Gifford et al. |
| 2004/0260271 A1 | 12/2004 | Huyser et al. |
| 2004/0260384 A1 | 12/2004 | Allen |
| 2004/0267348 A1 | 12/2004 | Gunderson et al. |
| 2005/0033403 A1 | 2/2005 | Ward et al. |
| 2005/0070794 A1 | 3/2005 | Deal et al. |
| 2005/0090802 A1 | 4/2005 | Connors et al. |
| 2005/0096724 A1 | 5/2005 | Stenzel et al. |
| 2005/0119719 A1 | 6/2005 | Wallace et al. |
| 2005/0125051 A1 | 6/2005 | Eidenschink et al. |
| 2005/0131449 A1 | 6/2005 | Salahieh et al. |
| 2005/0143773 A1 | 6/2005 | Abrams et al. |
| 2005/0149160 A1 | 7/2005 | Mcferran |
| 2005/0182388 A1 | 8/2005 | Garabedian et al. |
| 2005/0182475 A1 | 8/2005 | Jen et al. |
| 2005/0228361 A1 | 10/2005 | Tremaglio |
| 2005/0240254 A1 | 10/2005 | Austin |
| 2005/0267563 A1 | 12/2005 | Case et al. |
| 2005/0273149 A1 | 12/2005 | Tran et al. |
| 2005/0277949 A1 | 12/2005 | Que et al. |
| 2006/0030835 A1 | 2/2006 | Sherman et al. |
| 2006/0036309 A1 | 2/2006 | Hebert et al. |
| 2006/0058865 A1 | 3/2006 | Case et al. |
| 2006/0064123 A1 | 3/2006 | Bonnette et al. |
| 2006/0074477 A1 | 4/2006 | Berthiaume et al. |
| 2006/0089618 A1 | 4/2006 | Mcferran et al. |
| 2006/0095050 A1 | 5/2006 | Hartley et al. |
| 2006/0100687 A1 | 5/2006 | Fahey et al. |
| 2006/0100688 A1 | 5/2006 | Jordan et al. |
| 2006/0116750 A1 | 6/2006 | Hebert et al. |
| 2006/0129166 A1 | 6/2006 | Lavelle |
| 2006/0178698 A1 | 8/2006 | Mcintyre et al. |
| 2006/0184226 A1 | 8/2006 | Austin |
| 2006/0212042 A1 | 9/2006 | Amport et al. |
| 2006/0217682 A1 | 9/2006 | Stivland et al. |
| 2006/0235502 A1 | 10/2006 | Belluche et al. |
| 2006/0271093 A1* | 11/2006 | Holman ............... A61M 25/10 606/194 |
| 2007/0027520 A1 | 2/2007 | Sherburne |
| 2007/0043430 A1 | 2/2007 | Stinson |
| 2007/0049903 A1 | 3/2007 | Jansen et al. |
| 2007/0078504 A1 | 4/2007 | Mialhe |
| 2007/0088323 A1 | 4/2007 | Campbell et al. |
| 2007/0100421 A1 | 5/2007 | Griffin |
| 2007/0117645 A1 | 5/2007 | Nakashima |
| 2007/0129706 A1 | 6/2007 | Katoh et al. |
| 2007/0149927 A1 | 6/2007 | Itou et al. |
| 2007/0161956 A1 | 7/2007 | Heuser |
| 2007/0185446 A1 | 8/2007 | Accisano |
| 2007/0203563 A1 | 8/2007 | Hebert et al. |
| 2007/0233224 A1 | 10/2007 | Leynov et al. |
| 2007/0239254 A1 | 10/2007 | Chia et al. |
| 2007/0239261 A1 | 10/2007 | Bose et al. |
| 2007/0250039 A1 | 10/2007 | Lobbins et al. |
| 2007/0250040 A1 | 10/2007 | Provost et al. |
| 2007/0255255 A1 | 11/2007 | Shah et al. |
| 2007/0255388 A1 | 11/2007 | Rudakov et al. |
| 2007/0270779 A1 | 11/2007 | Jacobs et al. |
| 2007/0299424 A1 | 12/2007 | Cumming et al. |
| 2007/0299500 A1 | 12/2007 | Hebert et al. |
| 2007/0299501 A1 | 12/2007 | Hebert et al. |
| 2007/0299502 A1 | 12/2007 | Hiebert et al. |
| 2008/0009934 A1 | 1/2008 | Schneider et al. |
| 2008/0015558 A1 | 1/2008 | Harlan |
| 2008/0015678 A1 | 1/2008 | Kaplan et al. |
| 2008/0027528 A1 | 1/2008 | Jagger et al. |
| 2008/0033399 A1 | 2/2008 | Hunn et al. |
| 2008/0033528 A1 | 2/2008 | Satasiya et al. |
| 2008/0051705 A1 | 2/2008 | Von et al. |
| 2008/0051761 A1 | 2/2008 | Slazas et al. |
| 2008/0071301 A1 | 3/2008 | Matsuura et al. |
| 2008/0077229 A1 | 3/2008 | Andreas et al. |
| 2008/0082083 A1 | 4/2008 | Forde et al. |
| 2008/0091169 A1 | 4/2008 | Heideman et al. |
| 2008/0097398 A1 | 4/2008 | Mitelberg et al. |
| 2008/0108974 A1 | 5/2008 | Yee |
| 2008/0132933 A1 | 6/2008 | Gerber |
| 2008/0132989 A1* | 6/2008 | Snow ............... A61F 2/966 623/1.42 |
| 2008/0140180 A1 | 6/2008 | Dolan et al. |
| 2008/0147001 A1 | 6/2008 | Al-Marashi et al. |
| 2008/0147162 A1 | 6/2008 | Andreas et al. |
| 2008/0177249 A1 | 7/2008 | Heuser et al. |
| 2008/0188865 A1 | 8/2008 | Miller et al. |
| 2008/0188928 A1 | 8/2008 | Salahieh et al. |
| 2008/0221666 A1 | 9/2008 | Licata et al. |
| 2008/0234660 A2 | 9/2008 | Cumming et al. |
| 2008/0234795 A1 | 9/2008 | Snow et al. |
| 2008/0243225 A1 | 10/2008 | Satasiya et al. |
| 2008/0255541 A1 | 10/2008 | Hoffman et al. |
| 2008/0255653 A1 | 10/2008 | Schkolnik |
| 2008/0255654 A1 | 10/2008 | Hebert et al. |
| 2008/0262471 A1 | 10/2008 | Warnock |
| 2008/0262472 A1 | 10/2008 | Lunn et al. |
| 2008/0262592 A1 | 10/2008 | Jordan et al. |
| 2008/0275426 A1 | 11/2008 | Holman et al. |
| 2008/0300667 A1 | 12/2008 | Hebert et al. |
| 2008/0312639 A1 | 12/2008 | Weber |
| 2009/0012500 A1 | 1/2009 | Murata et al. |
| 2009/0082609 A1 | 3/2009 | Condado |
| 2009/0105802 A1 | 4/2009 | Henry et al. |
| 2009/0125053 A1 | 5/2009 | Ferrera et al. |
| 2009/0132019 A1 | 5/2009 | Duffy et al. |
| 2009/0138066 A1 | 5/2009 | Leopold et al. |
| 2009/0143849 A1 | 6/2009 | Ozawa et al. |
| 2009/0149835 A1 | 6/2009 | Velasco et al. |
| 2009/0157048 A1 | 6/2009 | Sutermeister et al. |
| 2009/0160112 A1 | 6/2009 | Ostrovsky |
| 2009/0171319 A1 | 7/2009 | Guo et al. |
| 2009/0204196 A1 | 8/2009 | Weber |
| 2009/0240235 A1 | 9/2009 | Murata |
| 2009/0264985 A1 | 10/2009 | Bruszewski |
| 2009/0287182 A1 | 11/2009 | Bishop et al. |
| 2009/0287183 A1 | 11/2009 | Bishop et al. |
| 2009/0287187 A1 | 11/2009 | Legaspi et al. |
| 2009/0287292 A1 | 11/2009 | Becking et al. |
| 2009/0299333 A1 | 12/2009 | Wendlandt et al. |
| 2009/0299449 A1 | 12/2009 | Styrc |
| 2009/0318947 A1 | 12/2009 | Garcia et al. |
| 2010/0020354 A1 | 1/2010 | Ito |
| 2010/0036363 A1 | 2/2010 | Watanabe et al. |
| 2010/0049293 A1 | 2/2010 | Zukowski et al. |
| 2010/0049297 A1 | 2/2010 | Dorn |
| 2010/0057184 A1 | 3/2010 | Randolph et al. |
| 2010/0057185 A1 | 3/2010 | Melsheimer et al. |
| 2010/0069852 A1 | 3/2010 | Kelley |
| 2010/0087913 A1 | 4/2010 | Rabkin et al. |
| 2010/0094258 A1 | 4/2010 | Shimogami et al. |
| 2010/0094394 A1 | 4/2010 | Beach et al. |
| 2010/0094395 A1 | 4/2010 | Kellett |
| 2010/0100106 A1 | 4/2010 | Ferrera |
| 2010/0160863 A1 | 6/2010 | Heuser |
| 2010/0198334 A1 | 8/2010 | Yodfat et al. |
| 2010/0204770 A1 | 8/2010 | Mas et al. |
| 2010/0217235 A1 | 8/2010 | Thorstenson et al. |
| 2010/0256602 A1 | 10/2010 | Lippert et al. |
| 2010/0256603 A1 | 10/2010 | Lippert et al. |
| 2010/0262157 A1 | 10/2010 | Silver et al. |
| 2010/0268243 A1 | 10/2010 | Parker |
| 2010/0268328 A1 | 10/2010 | Stiger |
| 2010/0274270 A1 | 10/2010 | Patel et al. |
| 2010/0298931 A1 | 11/2010 | Quadri et al. |
| 2010/0331951 A1 | 12/2010 | Bei et al. |
| 2011/0009943 A1 | 1/2011 | Paul et al. |
| 2011/0022157 A1 | 1/2011 | Essinger et al. |
| 2011/0029065 A1 | 2/2011 | Wood et al. |
| 2011/0034987 A1 | 2/2011 | Kennedy |
| 2011/0054586 A1 | 3/2011 | Mayberry et al. |

(56) References Cited

U.S. PATENT DOCUMENTS

| | | |
|---|---|---|
| 2011/0093055 A1 | 4/2011 | Kujawski |
| 2011/0098804 A1 | 4/2011 | Yeung et al. |
| 2011/0106235 A1 | 5/2011 | Haverkost et al. |
| 2011/0112623 A1 | 5/2011 | Schatz |
| 2011/0137403 A1 | 6/2011 | Rasmussen et al. |
| 2011/0152760 A1 | 6/2011 | Parker |
| 2011/0160763 A1 | 6/2011 | Ferrera et al. |
| 2011/0178588 A1 | 7/2011 | Haselby |
| 2011/0190862 A1 | 8/2011 | Bashiri et al. |
| 2011/0190865 A1 | 8/2011 | Mchugo et al. |
| 2011/0208292 A1 | 8/2011 | Von et al. |
| 2011/0224650 A1 | 9/2011 | Itou et al. |
| 2011/0257720 A1 | 10/2011 | Peterson et al. |
| 2011/0288626 A1 | 11/2011 | Straubinger et al. |
| 2011/0319904 A1 | 12/2011 | Hollett et al. |
| 2012/0029607 A1 | 2/2012 | Mchugo et al. |
| 2012/0035700 A1 | 2/2012 | Leanna et al. |
| 2012/0053681 A1 | 3/2012 | Alkhatib et al. |
| 2012/0059449 A1 | 3/2012 | Dorn et al. |
| 2012/0065660 A1 | 3/2012 | Ferrera et al. |
| 2012/0116494 A1 | 5/2012 | Leynov et al. |
| 2012/0123511 A1 | 5/2012 | Brown |
| 2012/0226343 A1 | 9/2012 | Vo et al. |
| 2012/0253447 A1 | 10/2012 | Hayasaka et al. |
| 2012/0316638 A1 | 12/2012 | Grad et al. |
| 2013/0085562 A1 | 4/2013 | Rincon et al. |
| 2013/0131775 A1 | 5/2013 | Hadley et al. |
| 2013/0172925 A1 | 7/2013 | Garcia et al. |
| 2013/0172979 A1 | 7/2013 | Fargahi |
| 2013/0226276 A1 | 8/2013 | Newell et al. |
| 2013/0226278 A1 | 8/2013 | Newell et al. |
| 2013/0261730 A1 | 10/2013 | Bose et al. |
| 2013/0274618 A1 | 10/2013 | Hou et al. |
| 2013/0274855 A1 | 10/2013 | Stante et al. |
| 2013/0274859 A1 | 10/2013 | Argentine |
| 2013/0282099 A1 | 10/2013 | Huynh |
| 2013/0304185 A1 | 11/2013 | Newell et al. |
| 2014/0025150 A1 | 1/2014 | Lim |
| 2014/0031918 A1 | 1/2014 | Newell et al. |
| 2014/0094929 A1* | 4/2014 | Shin .............. A61F 2/848 623/23.66 |
| 2014/0148893 A1 | 5/2014 | Kusleika |
| 2014/0171826 A1 | 6/2014 | Lampropoulos et al. |
| 2014/0172067 A1 | 6/2014 | Brown et al. |
| 2014/0194919 A1 | 7/2014 | Losordo et al. |
| 2014/0200648 A1 | 7/2014 | Newell et al. |
| 2014/0276541 A1 | 9/2014 | Ahluwalia et al. |
| 2014/0277332 A1 | 9/2014 | Slazas et al. |
| 2015/0032198 A1 | 1/2015 | Folk |
| 2015/0066128 A1 | 3/2015 | Losordo et al. |
| 2015/0066129 A1 | 3/2015 | Nageswaran et al. |
| 2015/0066130 A1 | 3/2015 | Haggstrom et al. |
| 2015/0066131 A1 | 3/2015 | Luong et al. |
| 2015/0080937 A1 | 3/2015 | Davidson |
| 2015/0133990 A1 | 5/2015 | Davidson |
| 2015/0164666 A1 | 6/2015 | Johnson et al. |
| 2015/0238336 A1 | 8/2015 | Johnson et al. |
| 2016/0113793 A1 | 4/2016 | Nishigishi |
| 2016/0206454 A1 | 7/2016 | Fischell et al. |
| 2017/0035592 A1 | 2/2017 | Haggstrom et al. |
| 2017/0252161 A1 | 9/2017 | Tran et al. |
| 2018/0042745 A1 | 2/2018 | Losordo et al. |
| 2018/0200092 A1 | 7/2018 | Nageswaran et al. |
| 2018/0263799 A1 | 9/2018 | Elwood et al. |
| 2018/0311061 A1 | 11/2018 | Nolan et al. |
| 2019/0151124 A1* | 5/2019 | Hammersmark ....... A61F 2/966 |
| 2019/0314175 A1 | 10/2019 | Dawson et al. |
| 2019/0314176 A1 | 10/2019 | Nageswaran et al. |
| 2019/0314177 A1 | 10/2019 | Alonso et al. |
| 2019/0314179 A1 | 10/2019 | Nageswaran et al. |
| 2019/0336312 A1 | 11/2019 | Nageswaran et al. |
| 2019/0374358 A1 | 12/2019 | Nageswaran |
| 2020/0375769 A1 | 12/2020 | Nageswaran et al. |
| 2020/0405517 A1 | 12/2020 | Barooni |
| 2021/0196490 A1 | 7/2021 | Dawson et al. |
| 2022/0257396 A1 | 8/2022 | Ashby et al. |
| 2023/0038177 A1 | 2/2023 | Deen et al. |

FOREIGN PATENT DOCUMENTS

| | | |
|---|---|---|
| EP | 1344502 A2 | 9/2003 |
| JP | 2001504016 A | 3/2001 |
| JP | 2008518717 A | 6/2008 |
| JP | 2009542357 A | 12/2009 |
| JP | 2013500777 A | 1/2013 |
| JP | 2013158647 A | 8/2013 |
| WO | 9719713 A2 | 6/1997 |
| WO | 9820811 A1 | 5/1998 |
| WO | 2010127838 A2 | 11/2010 |
| WO | 2011076408 A1 | 6/2011 |
| WO | 2011081997 A1 | 7/2011 |
| WO | 2011122444 A1 | 10/2011 |
| WO | 2012158152 A1 | 11/2012 |
| WO | 2014074462 A2 | 5/2014 |
| WO | 2020072268 A1 | 4/2020 |

OTHER PUBLICATIONS

Stoeckel et al., "Self-expanding nitinol stents: material and design considerations", Eur Radiol (2004) 14:292-301. (Year: 2003).*

International Search Report and Written Opinion mailed May 23, 2022, International Application No. PCT/US2022/012747, 15 pages.

International Search Report and Written Opinion mailed Oct. 15, 2020, International Application No. PCT/US20/70151, 110 pages.

Search Report dated Mar. 24, 2020, CN Application No. 201880007614. 9, 10 pages.

* cited by examiner

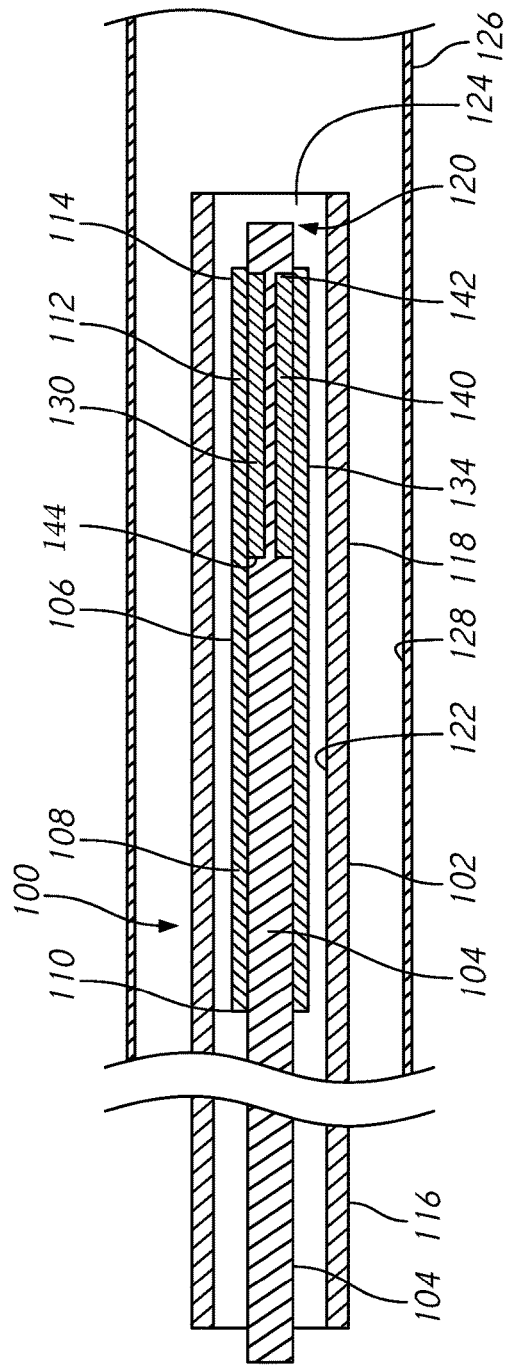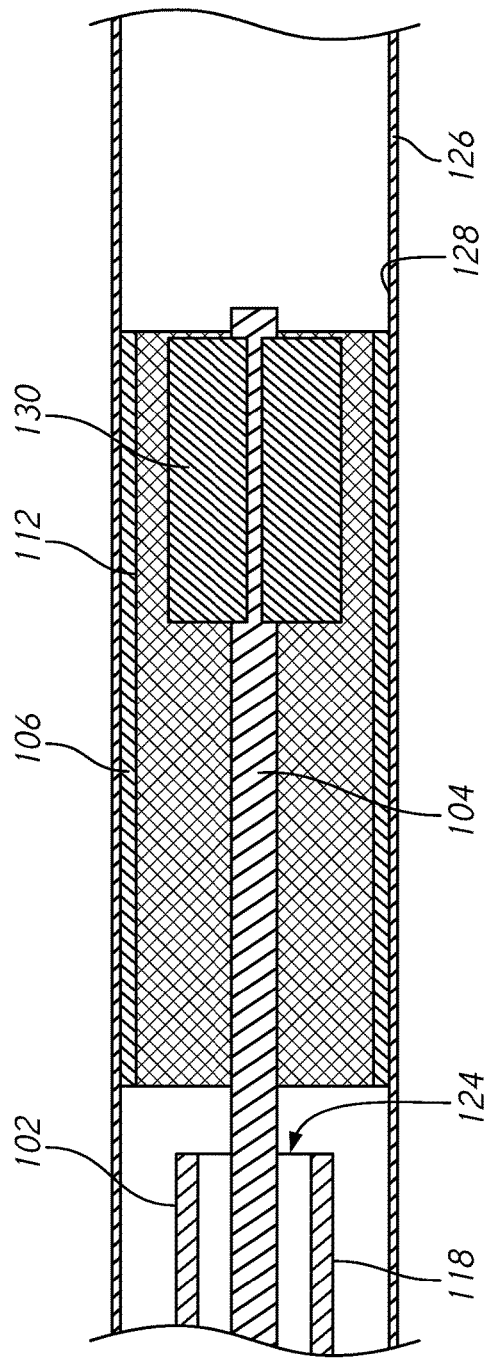
FIG. 1A
FIG. 1B

MEDICAL DEVICE DELIVERY

TECHNICAL FIELD

The present technology relates to medical device delivery devices, systems, and methods.

BACKGROUND

Walls of the vasculature, particularly arterial walls, may develop areas of pathological dilatation called aneurysms that often have thin, weak walls that are prone to rupturing. Aneurysms are generally caused by weakening of the vessel wall due to disease, injury, or a congenital abnormality. Aneurysms occur in different parts of the body, and the most common are abdominal aortic aneurysms and cerebral (e.g., brain) aneurysms in the neurovasculature. When the weakened wall of an aneurysm ruptures, it can result in death, especially if it is a cerebral aneurysm that ruptures.

Aneurysms are generally treated by excluding or at least partially isolating the weakened part of the vessel from the arterial circulation. For example, conventional aneurysm treatments include: (i) surgical clipping, where a metal clip is secured around the base of the aneurysm; (ii) packing the aneurysm with small, flexible wire coils (micro-coils); (iii) using embolic materials to "fill" an aneurysm; (iv) using detachable balloons or coils to occlude the parent vessel that supplies the aneurysm; and (v) intravascular stenting.

Intravascular stents are well known in the medical arts for the treatment of vascular stenoses or aneurysms. Stents are prostheses that expand radially or otherwise within a vessel or lumen to support the vessel from collapsing. Methods for delivering these intravascular stents are also well known.

Conventional methods of introducing a compressed stent into a vessel and positioning it within an area of stenosis or an aneurysm include percutaneously advancing a distal portion of a guiding catheter through the vascular system of a patient until the distal portion is proximate the stenosis or aneurysm. A second, inner catheter and a guidewire within the inner catheter are advanced through the distal region of the guiding catheter. The guidewire is then advanced out of the distal region of the guiding catheter into the vessel until the distal portion of the guidewire carrying the compressed stent is positioned at the point of the lesion within the vessel. The compressed stent is then released and expanded so that it supports the vessel at the point of the lesion.

SUMMARY

The present technology is illustrated, for example, according to various aspects described below. Various examples of aspects of the present technology are described as alternative embodiments. These are provided as examples and do not limit the present technology.

According to one aspect of the present technology, a stent delivery system includes a core member configured for advancement within a corporeal lumen and an expandable member positioned on the core member, wherein the expandable member is adapted to be radially expanded from a collapsed delivery configuration to an expanded configuration. The system also includes a stent extending along the core member and over the expandable member, the stent comprising a stent delivery configuration wherein the stent is radially compressed against the core member, comprising a stent expanded configuration wherein the stent is radially expanded from the stent delivery configuration. The stent has a primary set configuration toward which the stent is biased wherein the stent is radially larger than the stent expanded configuration, and a secondary set configuration toward which the stent is biased wherein the stent is radially compressed smaller than the stent delivery configuration.

In some embodiments, the expandable member comprises a first end secured to the core member, a second end slidingly secured to the core member, wherein relative movement of the first end toward the second end causes the expandable member to shorten and radially expand, and wherein relative movement of the first end away from the second end causes the expandable member to lengthen and radially compress. In some embodiments, the first end is fixedly secured to the core member. Optionally, the first end is distal to the second end, or alternatively the first end can be proximal of the second end. The expandable member can include a main body having a cylindrical shape when the expandable member is in the collapsed delivery configuration. In various embodiments, the expandable member comprises a slotted hypotube, a laser-cut structure, a braided structure, and/or is self-expanding or selectively expandable (e.g., via an actuator).

In some embodiments, while in the delivery state, the expandable member contacts the stent along less than the entire length of the stent. The system can further include a catheter through which the core member and stent are configured to be slidably advanced. The stent can be formed of a shape memory material (e.g., a shape-memory metal, a shape-memory polymer, etc.). In some embodiments, the stent can be heat-set into the primary set configuration and/or heat-set into the secondary stent configuration.

In another aspect, a stent delivery system includes a core member configured for advancement within a corporeal lumen, an expandable member coupled to the core member, and a stent extending along the core member and over the expandable member. The stent has stent delivery configuration wherein the stent is radially compressed against the core member and comprises a maximum stent delivery diameter, wherein the stent is characterized by the memory material having a secondary set configuration wherein the stent is radially compressed and comprises a secondary stent maximum diameter which is no greater than the maximum stent delivery diameter, and wherein the stent is further characterized by the memory material having a primary set configuration wherein the stent is radially expanded and comprises a primary set maximum diameter which is greater than the maximum stent delivery diameter.

In some embodiments, the stent is adapted to be deployed within a body lumen, wherein the stent after deployment in the body lumen comprises a stent expanded configuration wherein the stent is radially expanded against a wall of the body lumen and wherein the stent comprises a maximum stent expanded diameter which is no greater than the primary set maximum diameter. The stent can be formed of a shape memory material, a shape memory metal, and/or a shape memory polymer. The stent can be heat-set into the primary set configuration and/or heat-set into the secondary set configuration.

According to another aspect of the present technology, a method of manufacturing a stent delivery system includes providing a stent formed from a memory material, setting the stent into a primary set configuration, wherein the primary stent configuration has a primary set configuration minimum stent diameter, and setting the stent into a secondary set configuration. In the secondary stent configuration, the stent has a secondary set configuration minimum stent diameter, wherein the secondary set configuration minimum stent diameter is less than the primary set configuration minimum stent diameter. The method further includes sliding the stent over a stent-receiving surface of an elongated core member, wherein the elongated core member is adapted to be distally advanced through a body lumen of a patient to thereby advance the stent-receiving surface to a desired treatment site in the patient, and securing the stent to the stent-receiving surface of the elongated core member.

In some embodiments, securing the stent to the stent-receiving surface comprises reducing the diameter of the stent until an inner surface of the stent engages the stent-receiving surface. Reducing the diameter of the stent can include reducing the stent to a compressed minimum diameter which is larger than the secondary set configuration minimum stent diameter. Additionally or alternatively, reducing the diameter of the stent can include applying a compressive force onto a radially outer surface of the stent to thereby radially compress the stent onto the stent-receiving surface of the core member.

In some embodiments, the method further includes placing the stent over a hollow mandrel, wherein the hollow mandrel has a mandrel outer diameter sufficient to hold the stent in a configuration wherein the stent is biased toward the secondary stent configuration, and the hollow mandrel has a mandrel inner lumen of sufficient size to slidingly receive therein a portion of the core member on which the stent-receiving surface is positioned. Sliding the stent over the elongated core member can include sliding the hollow mandrel over the stent-receiving surface of the elongated core member, and wherein reducing the diameter of the stent comprises slidingly removing the stent from off of the mandrel while simultaneously maintaining the stent in position over the stent-receiving surface and while also slidingly removing the mandrel from off of the stent-receiving surface of the elongated core member, whereupon the stent will radially collapse toward the secondary configuration minimum stent diameter until the inner surface of the stent engages the stent-receiving surface.

In some embodiments, the method further includes mechanically deforming the stent into a stent mounting configuration wherein an inner lumen of the stent is adapted to slidingly receive the stent-receiving surface of the core member therein, wherein mechanically deforming the stent into the stent mounting configuration occurs prior to sliding the stent over the stent-receiving surface of the elongated core member. The method can further include exposing the stent to a temperature sufficient to cause the stent to be biased away from the stent mounting configuration and to be biased toward the stent secondary configuration.

According to another aspect of the present technology, a stent includes a stent main body formed from a shape memory material and configured to be percutaneously advanced through one or more body lumens of a patient to a target site in a patient's body. The stent main body has a primary set configuration wherein the stent main body comprises a stent primary set maximum diameter and a secondary set configuration wherein the stent main body comprises a stent secondary set maximum outer diameter, wherein the stent primary set maximum outer diameter is greater than the stent secondary set maximum outer diameter.

In some embodiments, the memory material comprises a memory metal and/or a memory polymer. The stent can be biased toward the primary set configuration when the stent is exposed to a temperature at least as high as a primary activation temperature. The stent can be biased toward the secondary set configuration when the stent is exposed to a temperature at least as high as a secondary activation temperature. In some embodiments, the stent is biased toward the primary set configuration when the stent is exposed to the temperature of the patient's body. In some embodiments, the stent primary set maximum outer diameter is at least as large as a largest diameter of the target site in the patient's body.

According to another aspect of the present technology, a method of delivering a stent to a treatment site in a patient's body includes providing a medical device delivery system. The system includes an elongated core member having a core member distal portion with a medical device releasably secured to the core member distal portion, the medical device characterized in having a first set configuration wherein the medical device has a first set maximum diameter, and further characterized in having a second set configuration wherein the medical device has a second set maximum diameter, the medical device further characterized in having a delivery configuration in which the medical device is releasably secured to the core member distal portion. The method further includes advancing the core member distal portion with stent thereon through one or more of the patient's body lumens to a treatment site in the patient's body, releasing the medical device from the core member distal portion, and radially expanding the medical device from the delivery configuration to a deployed configuration, whereby the medical device is deployed at the treatment site.

Additional features and advantages of the present technology will be set forth in the description below, and in part will be apparent from the description, or may be learned by practice of the subject technology. The advantages of the present technology will be realized and attained by the structure particularly pointed out in the written description and claims hereof as well as the appended drawings.

It is to be understood that both the foregoing general description and the following detailed description are exemplary and explanatory and are intended to provide further explanation of the present technology as claimed.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

FIGS. 1A and 1B are side cross-sectional illustrations of a medical device delivery system configured in accordance with some embodiments.

DETAILED DESCRIPTION

Figure 2:
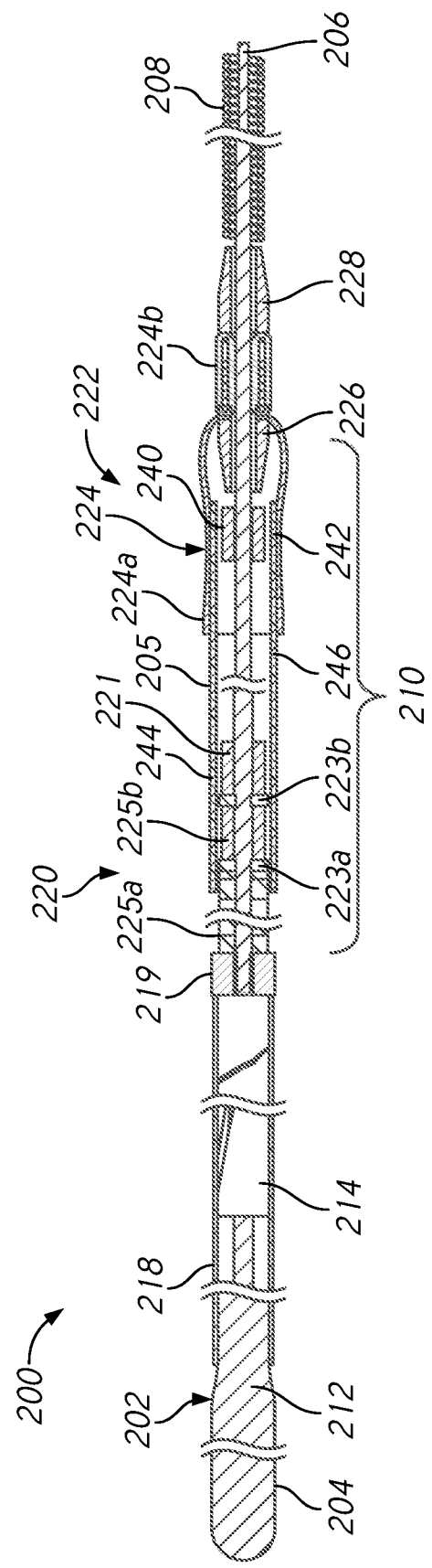
FIG. 2 is a side, cross-sectional view of a medical device delivery system, according to some embodiments.

Self-expanding stents may be advanced into vascular vessels while mounted on a core member, but typically require radial restraint, such as provided by a restraining sheath or surrounding catheter, that prevents unwanted expansion of the self-expanding stent during advancement through a body lumen to a deployment site. In many neurovascular applications and other areas where a stent is advanced into relatively narrow and/or relatively fragile body lumens, the stent can be restrained onto the core member by the inner wall of a catheter through which the core member and stent are advanced. The radially outward force created by a self-expanding stent against the catheter inner wall can make advancement of the stent and core member through and/or out of the catheter difficult due to the friction created by the self-expanding stent pressing radially outwardly toward the catheter inner wall.

A stent formed from a memory material, such as Nitinol, may have a primary set (e.g., heat set) of the stent that sets the stent in an expanded configuration, which permits the stent to radially expand and remain in a desired deployed configuration when deployed at a treatment site. A secondary set (e.g., heat set) of the stent may be added in order to set the stent in a compressed configuration, which helps the stent remain compressed in a delivery configuration against the core member and reduces friction between the stent and the catheter walls through which the stent is advanced, thus reducing the delivery force (i.e., the "pushing" force needed to advance the stent and core member through and out of the catheter lumen). To urge the stent from the delivery configuration toward the deployed configuration, a radially expandable component may be positioned on the core member which may be selectively radially expanded. At least a portion of the stent may be mounted over the radially expandable member, with the radially expandable member adapted to radially expand the stent from the delivery configuration and into the deployed configuration, so that the deployed stent properly engages the body lumen walls upon and after deployment. Expansion of the radially expandable member may be selectively controlled, such as by a wire that when pulled can reduce the length of the radially expandable member, thereby increasing the diameter thereof.

Specific details of several embodiments of the present technology are described herein with reference to FIGS. 1-11B. Although many of the embodiments are described with respect to devices, systems, and methods for delivery of stents, tubular implants such as filters, shunts or stent-grafts and other medical devices, other applications and other embodiments in addition to those described herein are within the scope of the present technology, and can be employed in any of the embodiments of systems disclosed herein, in place of a stent as is typically disclosed. It should be noted that other embodiments in addition to those disclosed herein are within the scope of the present technology. Further, embodiments of the present technology can have different configurations, components, and/or procedures than those shown or described herein. Moreover, embodiments of the present technology can have configurations, components, and/or procedures in addition to those shown or described herein and that these and other embodiments may not have several of the configurations, components, and/or procedures shown or described herein without deviating from the present technology.

As used herein, the terms "distal" and "proximal" define a position or direction with respect to a clinician or a clinician's control device (e.g., a handle of a delivery catheter). For example, the terms, "distal" and "distally" refer to a position distant from or in a direction away from a clinician or a clinician's control device along the length of device. In a related example, the terms "proximal" and "proximally" refer to a position near or in a direction toward a clinician or a clinician's control device along the length of device. The headings provided herein are for convenience only and should not be construed as limiting the subject matter disclosed.

Selected Examples of Medical Device Delivery Systems

FIGS. 1A— 2 depict embodiments of medical device delivery systems that may be used to deliver and/or deploy a medical device, such as but not limited to a stent, into a hollow anatomical structure such as a blood vessel. The stent can comprise a braided stent or other form of stent such as a woven stent, knit stent, laser-cut stent, roll-up stent, etc. The stent can optionally be configured to act as a "flow diverter" device for treatment of aneurysms, such as those found in blood vessels including arteries in the brain or within the cranium, or in other locations in the body such as peripheral arteries. The stent can optionally be similar to any of the versions or sizes of the PIPELINE™ Embolization Device marketed by Medtronic Neurovascular of Irvine, California USA. The stent can alternatively comprise any suitable tubular medical device and/or other features, as described herein. In some embodiments, the stent can be any one of the stents described in U.S. application Ser. No. 15/892,268, filed Feb. 8, 2018, titled VASCULAR EXPANDABLE DEVICES, the entirety of which is hereby incorporated by reference herein and made a part of this specification.

FIG. 1A is a schematic illustration of a medical device delivery system 100 configured in accordance with an embodiment of the present technology. The system 100 can comprise an elongate tube or catheter 102 which slidably receives a core member or core assembly 104 configured to carry a stent 106 through the catheter 102. The depicted stent 106 has a stent proximal region 108 with a stent proximal end 110, and an opposing stent distal region 112 with a stent distal end 114. The depicted catheter 102 has a catheter proximal region 116 and an opposing catheter distal region 118 which can be positioned at a treatment site within a patient, an internal lumen 120 extending from the catheter proximal region 116 to the catheter distal region 118, and an inner wall surface 122 defining the internal lumen 120. At the catheter distal region 118, the catheter 102 has a distal opening 124 through which the core member 104 may be advanced beyond the catheter distal region 118 to expand or deploy the stent 106 within the body lumen 126 so that the stent 106 engages the body lumen wall 128. The catheter proximal region 116 may include a catheter hub (not shown) or catheter handle (not shown). The catheter 102 can define a generally longitudinal dimension extending between the catheter proximal region 116 and the catheter distal region 118. When the delivery system 100 is in use, the longitudinal dimension of the catheter 102 need not be straight along some or any of its length.

The core member 104 is configured to extend generally longitudinally through the lumen 120 of the catheter 102. The core member 104 can generally comprise any member(s) with sufficient flexibility and column strength to move the stent 106 or other medical device through the catheter 102. The core member 104 can therefore comprise a wire, tube (e.g., hypotube), braid, coil, or other suitable member(s), or a combination of wire(s), tube(s), braid(s), coil(s), etc.

An expandable member 130 may be positioned on the core member 104 at a position under at least a portion of the stent 106. The expandable member 130 may be adapted to be selectively radially expanded from a smaller delivery diameter to a larger deployment diameter. Note that a user may be able to selectively vary the size of the larger deployment diameter, such as via controls on a proximal portion (e.g., handle) (not shown) of the core member 104. The expandable member 130 may be adapted to be selectively radially compressed from the larger deployment diameter back down to a smaller diameter, such as to the smaller delivery diameter.

The radially expandable member 130 may be adapted to radially expand outwardly against the stent 106 to radially engage and releasably expand the stent 106 from the core member 104. The radially expandable member 130 may be formed with a main body 140 having a compressed configuration where the main body 140 is substantially cylindrical and lies close to the core member 104 as depicted in FIG. 1A. The radially expandable member 130 may have an expandable member distal end 142 and an expandable member proximal end 144. The expandable member 130 may be adapted to be selectively radially expanded to engage outwardly against the overlying portion of the stent 106.

As depicted in FIG. 1B, with the core member 104 distally advanced with respect to the catheter 102 such that the stent 106 is advanced out of the catheter distal opening 124, as depicted in FIG. 1B, a portion (such as a stent distal portion 112) or all of the stent 106 may radially expand into contact with the wall 128 of the body lumen 126. The distal restraining sheath 134 has been removed from the stent 106, which in the embodiment depicted involved sliding the distal restraining sheath 134 distally off of the stent 106. Radial expansion of the stent portion (or entirety) may be achieved by radial expansion of the radially expandable member 130. Note that the radially expandable member 130 may not expand to the full width of the body lumen, but can instead expand only enough to cause the stent 106 to reach a diameter where the stent is biased toward a larger diameter which is at least as large as, and maybe larger than, the width of the body lumen 126.

In operation, the stent 106 can be moved distally or proximally within the catheter 102 via the core member 104. To move the stent 106 out of the catheter distal opening 124, either the core member 104 is moved distally while the catheter 102 is held stationary, or the core member 104 is held stationary while the catheter 102 is withdrawn proximally, or the core member 104 is moved distally while the catheter 102 is withdrawn proximally. In each of these examples, the core member 104 is moved distally with respect to the catheter 102, such that the stent 106 is advanced distally with respect to the catheter 102, and ultimately out of the catheter distal region 118 and catheter distal opening 124. Conversely, to resheath or otherwise move the stent 106 back into the catheter 102, the relative movement between the core member 104 and the catheter 102 is reversed compared to moving the stent 106 out of the catheter 102. The resulting proximal movement of the stent 106 relative to the catheter 102 enables re-sheathing of the stent 106 back into the distal region 118 of the catheter 102. This is useful when the stent 106 has been partially deployed and a portion of the stent 106 remains disposed with some portion of the system, such as a proximal sheath on the core member 104. The stent 106 can thus be withdrawn back into the distal opening 124 of the catheter 102 by moving the core member 104 proximally relative to the catheter 102. Resheathing in this manner may remain possible until the entirety of the stent 106 is released from the core member and all other non-stent portions of the system.

The stent 106 can be coupled to the core member 104 using any suitable technique, including one or more restraining sheaths, one or more proximal bumpers or pushing elements configured to abut a proximal end of the stent 106, and/or one or more underlying stent engagement members configured to interlock with or otherwise engage the stent 106 and retain the stent 106 in position with respect to the overlying catheter 102.

In some embodiments, a distal restraining sheath (not shown) may be positioned distally of and extending over the stent distal portion 112, restraining the stent distal portion 112 to the core member 104. The distal restraining sheath may have a distal sheath distal end, which may be secured to the core member 104, and a distal sheath proximal end, which may be a free end and may be positioned over the stent distal portion 112. The distal restraining sheath may be adapted to be removed from the stent distal portion 112, such as by sliding distally and/or everting the distal sheath proximal end (aka the free end) toward and potentially distally of the distal sheath distal end (aka the fixed end), thereby releasing the stent distal portion 112 to radially expand outwardly from the core member 104.

Additionally or alternatively, a proximal restraining sheath (not shown) may be included, in addition to or in lieu of a distal restraining sheath (depending on the particular application and system aspects). The proximal restraining sheath can have similar features (e.g., proximal sheath proximal end secured to core member 104, proximal sheath distal end as a free end positioned over stent proximal portion 108, adapted to slide proximally or evert from off the stent 106 to release the stent to expand, etc.).

Some embodiments of the medical delivery system may include spacers and/or stent engagement members and/or other elements such as those disclosed in U.S. patent application Ser. No. 15/951,779, filed Apr. 12, 2018, the entirety of which is hereby incorporated by reference herein and made a part of this specification.

Examples of stent engagement members and other elements are depicted in FIG. 2, which illustrates a side cross-sectional view of another embodiment of a medical device delivery system 200 configured in accordance with an embodiment of the present technology. The delivery system 200 can be configured to carry a stent (or other vascular implant or device) 205 thereon to be advanced through a surrounding catheter to a target site in a patient, similar to the operation described above with respect to FIGS. 1A-1B. (The surrounding catheter is omitted in FIG. 2 for clarity). The delivery system 200 can be advanced distally with respect to a distal end of the catheter to expand or deploy the stent 205 at the target site.

The delivery system 200 can be used with any number of catheters. For example, the catheter can optionally comprise any of the various lengths of the MARKSMAN™ catheter available from Medtronic Neurovascular of Irvine, California USA. The catheter can optionally comprise a microcatheter having an inner diameter of about 0.030 inches or less, and/or an outer diameter of 3 French or less near the distal region. Instead of or in addition to these specifications, the catheter can comprise a microcatheter which is configured to percutaneously access the internal carotid artery, or another location within the neurovasculature distal of the internal carotid artery.

The delivery system 200 can comprise a core member or core assembly 202 configured to extend generally longitudinally through the lumen of a catheter. The core member 202 can have a proximal region 204 and a distal region 206, which can optionally include a tip coil 208. The core member 202 can also comprise an intermediate portion 210 located between the proximal region 204 and the distal region 206. The intermediate portion 210 is the portion of the core member 202 onto or over which the stent 205 extends when the core member 202 is in the pre-deployment configuration as shown in FIG. 2.

The core member 202 can generally comprise any member(s) with sufficient flexibility and column strength to move a stent or other medical device through a surrounding catheter. The core member 202 can therefore comprise a wire, tube (e.g., hypotube), braid, coil, or other suitable member(s), or a combination of wire(s), tube(s), braid(s), coil(s), etc. The embodiment of the core member 202 depicted in FIG. 2 is of multi-member construction, comprising a wire 212 with a tube 214 surrounding the wire 212 along at least a portion of its length. An outer layer 218, which can comprise a layer of lubricious material such as PTFE (polytetrafluoroethylene or TEFLON™) or other lubricious polymers, can cover some or all of the tube 214 and/or wire 212. The wire 212 may taper or vary in diameter along some or all of its length. The wire 212 may include one or more fluorosafe markers (not shown), and such marker(s) may be located on a portion of the wire 212 that is not covered by the outer layer 218 (e.g., proximal of the outer layer 218). This portion of the wire 212 marked by the marker(s), and/or proximal of any outer layer 218, can comprise a bare metal outer surface.

The core member 202 can further comprise a proximal coupling assembly 220 and/or a distal interface assembly 222 that can interconnect the stent 205 with the core member 202. The proximal coupling assembly 220 can comprise one or more stent engagement members 223a-b (together "engagement members 223") that are configured to mechanically engage or interlock with the stent 205. In this manner, the proximal coupling assembly 220 cooperates with an overlying inner surface of a surrounding catheter (not shown) to grip the stent 205 such that the proximal coupling assembly 220 can move the stent 205 along and within the catheter, e.g., as the user pushes the core member 202 distally and/or pulls the core member proximally relative to the catheter, resulting in a corresponding distal and/or proximal movement of the stent 205 within the catheter lumen.

The proximal coupling assembly 220 can, in some embodiments, include proximal and distal restraints 219, 221 that are fixed to the core member 202 (e.g., to the wire 212 thereof in the depicted embodiment) so as to be immovable relative to the core member 202, either in a longitudinal/sliding manner or a radial/rotational manner. The proximal coupling assembly 220 can also include a plurality of stent engagement members 223 separated by spacers 225a–b (together "spacers 225"). The stent engagement members 223 and spacers 225 can be coupled to (e.g., mounted on) the core member 202 so that the proximal coupling assembly 220 can rotate about the longitudinal axis of the core member 202 (e.g., of the intermediate portion 210), and/or move or slide longitudinally along the core member 202. In some embodiments, the proximal restraint 219 comprises a substantially cylindrical body with an outer diameter that is greater than or equal to an outer diameter of the first spacer 225a. The distal restraint 221 can taper in the distal direction down towards the core member 202. This tapering can reduce the risk of the distal restraint 221 contacting an inner surface of the overlying stent 205, particularly during navigation of tortuous vasculature, in which the system 200 can assume a highly curved configuration. In some embodiments, the distal restraint 221 can have an outside diameter or other radially outermost dimension that is smaller than the outside diameter or other radially outermost dimension of the overall proximal coupling assembly 220, so that distal restraint 221 will tend not to contact the inner surface of the overlying stent 205.

In the proximal coupling assembly 220 shown in FIG. 2, the stent 205 can be moved distally or proximally within an overlying catheter (not shown) via the proximal coupling assembly 220. In some embodiments, the stent 205 can be resheathed via the proximal coupling assembly 220 after partial deployment of the stent 205 from a distal opening of the catheter. For example, the coupling assembly 220 can be configured to engage the stent 205, such as via mechanical interlock with the pores and filaments of the stent 205, abutment of the proximal end or edge of the stent 205, frictional engagement with an inner wall of the stent 205, or any combination of these modes of action. The coupling assembly 220 can therefore cooperate with an overlying inner surface of a catheter (such as the inner wall surface 122 of the catheter 102 of FIGS. 1A-1B) to grip and/or abut the stent 205 such that the coupling assembly 220 can move the stent 205 along and within the catheter, e.g., distal and/or proximal movement of the core member 202 relative to the catheter results in a corresponding distal and/or proximal movement of the stent 205 within the catheter lumen.

The proximal coupling assembly 220 can be configured and function so that the proximal restraint 219 can be made to function as a pushing element by appropriately sizing the outer diameter of the proximal restraint 219 and the length of the first spacer 225a, such that the distal face of the proximal restraint 219 abuts the proximal end or edge of the stent 205. When the proximal coupling element 220 is so arranged, the proximal restraint 219 can transmit at least some, or most or all, distally directed push force to the stent 205 during delivery, and the stent engagement member(s) 223 do not transmit any distally directed push force to the stent 205 during delivery (or transmit only a small portion of such force, or do so only intermittently). The stent engagement member(s) 223 can transmit proximally directed pull force to the stent 205 during retraction or resheathing, and the proximal restraint 219 can transmit no proximally directed pull force to the stent (or it may do so occasionally or intermittently, for example when a portion of the stent 205 becomes trapped between the outer edge of the proximal restraint 219 and the inner wall of the catheter). The first spacer 225a can optionally take the form of a solid tube when the proximal coupling assembly 220 includes a proximal restraint 219 configured as a pushing element.

Although the proximal coupling assembly 220 can be configured in such a manner, with the proximal restraint 219 abutting the stent 205 so that the proximal restraint 219 can be used as a pushing element, the coupling assembly 220 may entail use of the stent engagement members 223 for both distal (delivery) and proximal (resheathing) movement of the stent 205.

Optionally, the proximal edge of the proximal coupling assembly 220 can be positioned just distal of the proximal edge of the stent 205 when in the delivery configuration. In some such embodiments, this enables the stent 205 to be re-sheathed when as little as a few millimeters of the stent remains in the catheter. Therefore, with stents of typical length, resheathability of 75% or more can be provided (i.e., the stent can be re-sheathed when 75% or more of it has been deployed).

With continued reference to FIG. 2, the distal interface assembly 222 can comprise a distal engagement member 224 that can take the form of, for example, a distal device cover or distal stent cover (generically, a "distal cover"), though other configurations are contemplated. The distal engagement member 224 can be configured to reduce friction between the stent 205 (e.g., a distal portion thereof) and the inner surface of a surrounding catheter. For example, the distal engagement member 224 can be configured as a lubricious, flexible structure having a free first end or section 224a that can extend over at least a portion of the stent 205 and/or intermediate portion 210 of the core member 202, and a fixed second end or section 224b that can be coupled (directly or indirectly) to the core member 202.

The distal engagement member 224 can have a first or delivery position, configuration, or orientation in which the distal cover can extend proximally relative to the distal tip, or proximally from the second section 224b or its (direct or indirect) attachment to the core member 202, and at least partially surround or cover a distal portion of the stent 205. The distal engagement member 224 can be movable from the first or delivery orientation to a second or resheathing position, configuration, or orientation (not shown) in which the distal cover can be everted such that the first end 224a of the distal cover is positioned distally relative to the second end 224b of the distal engagement member 224 to enable the resheathing of the core member 202, either with the stent 205 carried thereby, or without the stent 205. As shown in FIG. 2, the first section 224a of the distal engagement member 224 can originate from the proximal end of the second section 224b. In another embodiment, the first section 224a can originate from the distal end of the second section 224b.

The distal engagement member 224 can be manufactured using a lubricious and/or hydrophilic material such as PTFE or Teflon®, but may be made from other suitable lubricious materials or lubricious polymers. The distal cover can also comprise a radiopaque material which can be blended into the main material (e.g., PTFE) to impart radiopacity. The distal engagement member 224 can have a thickness of between about 0.0005" and about 0.003". In some embodiments, the distal cover can be one or more strips of PTFE having a thickness of about 0.001".

The distal engagement member 224 (e.g., the second end 224b thereof) can be fixed to the core member 202 (e.g., to the wire 212 or distal tip thereof) so as to be immovable relative to the core member 202, either in a longitudinal/sliding manner or a radial/rotational manner. Alternatively, as depicted in FIG. 2, the distal engagement member 224 (e.g., the second end 224b thereof) can be coupled to (e.g., mounted on) the core member 202 so that the distal engagement member 224 can rotate about a longitudinal axis of the core member 202 (e.g., of the wire 212), and/or move or slide longitudinally along the core member. In such embodiments, the second end 224b can have an inner lumen that receives the core member 202 therein such that the distal engagement member 224 can slide and/or rotate relative to the core member 202. Additionally, in such embodiments, the distal interface assembly 222 can further comprise a proximal restraint 226 that is fixed to the core member 202 and located proximal of the (second end 224b of the) distal engagement member 224, and/or a distal restraint 228 that is fixed to the core member 202 and located distal of the (second end 224b of the) distal engagement member 224. The distal interface assembly 222 can comprise a radial gap between the outer surface of the core member 202 (e.g., of the wire 212) and the inner surface of the second end 224b. Such a radial gap can be formed when the second end 224b is constructed with an inner luminal diameter that is somewhat larger than the outer diameter of the corresponding portion of the core member 202. When present, the radial gap allows the distal engagement member 224 and/or second end 224b to rotate about the longitudinal axis of the core member 202 between the restraints 226, 228.

In some embodiments, one or both of the proximal and distal restraints 226, 228 can have an outside diameter or other radially outermost dimension that is smaller than the (e.g., pre-deployment) outside diameter or other radially outermost dimension of the distal engagement member 224, so that one or both of the restraints 226, 228 will tend not to bear against or contact the inner surface of the catheter during operation of the core member 202. Alternatively, it can be preferable to make the outer diameters of the restraints 226 and 228 larger than the largest radial dimension of the pre-deployment distal engagement member 224, and/or make the outer diameter of the proximal restraint 226 larger than the outer diameter of the distal restraint 228. This configuration allows easy and smooth retrieval of the distal engagement member 224 and the restraints 226, 228 back into the catheter post stent deployment.

In operation, the distal engagement member 224, and in particular the first section 224a, can generally cover and protect a distal region of the stent 205 as the stent 205 is moved distally through a surrounding catheter. The distal engagement member 224 may serve as a bearing or buffer layer that, for example, inhibits filament ends of the distal region of the stent 205 (where the stent comprises a braided stent) from contacting an inner surface of the catheter, which could damage the stent 205 and/or catheter, or otherwise compromise the structural integrity of the stent 205. Since the distal engagement member 224 may be made of a lubricious material, the distal engagement member 224 may exhibit a low coefficient of friction that allows the distal region of the stent to slide axially within the catheter with relative ease. The coefficient of friction between the distal cover and the inner surface of the catheter can be between about 0.02 and about 0.4. For example, in embodiments in which the distal cover and the catheter are formed from PTFE, the coefficient of friction can be about 0.04. Such embodiments can advantageously improve the ability of the core member 202 to pass through the catheter, especially in tortuous vasculature.

Structures other than the herein-described embodiments of the distal engagement member 224 may be used in the core member 202 and/or distal interface assembly 222 to cover or otherwise interface with the distal region of the stent 205. For example, a protective coil or other sleeve having a longitudinally oriented, proximally open lumen may be employed. In other embodiments, the distal interface assembly 222 can omit the distal engagement member 224, or the distal cover can be replaced with a component similar to the proximal coupling assembly 220. Where the distal engagement member 224 is employed, it can be connected to the distal tip coil 208 (e.g., by being wrapped around and enclosing some or all of the winds of the coil 208) or being adhered to or coupled to the outer surface of the coil by an adhesive or a surrounding shrink tube. The distal engagement member 224 can be coupled (directly or indirectly) to other portions of the core member 202, such as the wire 212.

In embodiments of the core member 202 that employ both a rotatable proximal coupling assembly 220 and a rotatable distal engagement member 224, the stent 205 can be rotatable with respect to the core member 202 about the longitudinal axis thereof, by virtue of the rotatable connections of the proximal coupling assembly 220 and distal engagement member 224. In such embodiments, the stent 205, proximal coupling assembly 220 and distal engagement member 224 can rotate together in this manner about the core member 202. When the stent 205 can rotate about the core member 202, the core member 202 can be advanced more easily through tortuous vessels as the tendency of the vessels to twist the stent 205 and/or core member 202 is negated by the rotation of the stent 205, proximal coupling assembly 220, and distal engagement member 224 about the core member 202. In addition, the required push force or delivery force is reduced, as the user's input push force is not diverted into torsion of the stent 205 and/or core member 202. The tendency of a twisted stent 205 and/or core member 202 to untwist suddenly or "whip" upon exiting tortuosity or deployment of the stent 205, and the tendency of a twisted stent to resist expansion upon deployment, are also reduced or eliminated. Further, in some such embodiments of the core member 202, the user can "steer" the core member 202 via the tip coil 208, particularly if the coil 208 is bent at an angle in its unstressed configuration. Such a coil tip can be rotated about a longitudinal axis of the system 200 relative to the stent, coupling assembly 220 and/or distal engagement member 224 by rotating the distal region 206 of the core member 202. Thus the user can point the coil tip 208 in the desired direction of travel of the core member 202, and upon advancement of the core member the tip will guide the core member in the chosen direction.

An expandable member 240 may be positioned on the core member 202 at a position under the stent. The expandable member 240 is adapted to be radially expanded, thereby causing at least a portion of the stent 205 to radially expand. The expandable member 240 may be positioned on the core member 202 so that the core member 240 underlies a distal portion 242 of the stent 205 (as in the example depicted in FIG. 2). The expandable member 240 may alternatively underlie any portion or even the entirety of the stent, such as the proximal portion 244 of the stent 205, an intermediate portion 246 of the stent 205, the entirety of the stent 205, etc. Multiple expandable members (each of which may be adapted to be selectively and independently expanded from the other of the expandable members) may be positioned under various portions of the stent 205, such as a distal expandable member positioned on the core member at a position under the distal portion 242 of the stent 205, a proximal expandable member positioned on the core member at a position under the proximal portion 244 of the stent 205, an intermediate expandable member positioned on the core member at a position under an intermediate portion 246 of the stent 205, etc.

Note that various components of the delivery system 200 of FIG. 2 can be incorporated into the delivery system 100 of FIGS. 1A-1B, and vice versa. For example, any of the disclosed embodiments of the expandable member 240 of the delivery system 200 can be employed as the expandable member 130 of the delivery system 100. Any of the embodiments of the coupling assembly 220 can be employed with the delivery system 100. Similarly, any of the embodiments of the stent engagement members 223 can be employed with the delivery system 100, and/or any of the embodiments of the spacers 225 can be employed with the delivery system 100. Although many embodiments discussed herein include two engagement members 223, in other embodiments the delivery system 200 can include three, four, or more engagement members separated from one another by additional spacers. The spacing of such additional engagement members can be regular or irregular. For example, in one embodiment a third engagement member can be provided at a position configured to engage a distal region of the overlying stent, while the first and second engagement members engage only a proximal region of the overlying stent.

Additional Examples of Stents

In various embodiments, the stents can take different forms. For example, the shapes and sizes (e.g., lengths and/or diameters) of the stent (in primary, secondary, delivery or deployed configurations), the operational aspects of the stent (e.g., self-expanding, heat-set, etc.), the construction techniques (e.g., braided, laser-cut, etc.), the position of the expandable stent on the core member, the methods and mechanisms by which the stent is expanded/deployed, the methods by which the stent is secured to and released from the core member, and the material selected can all vary to achieve desired operation of the stent. FIGS. 3A-8B illustrate various alternative embodiments of stents. These stents can be incorporated into and combined with the systems and core members and stents described above with respect to FIGS. 1A-2. Additionally, aspects of these stents can be combined and intermixed such that features of any one of these stents (e.g., the diameters, configuration, mechanism of expansion, etc.) can be combined with the features of any of the other delivery systems and/or expandable members disclosed herein (e.g., the type of expandable member, type of delivery system (such as core member), etc.).

Figure 3A:
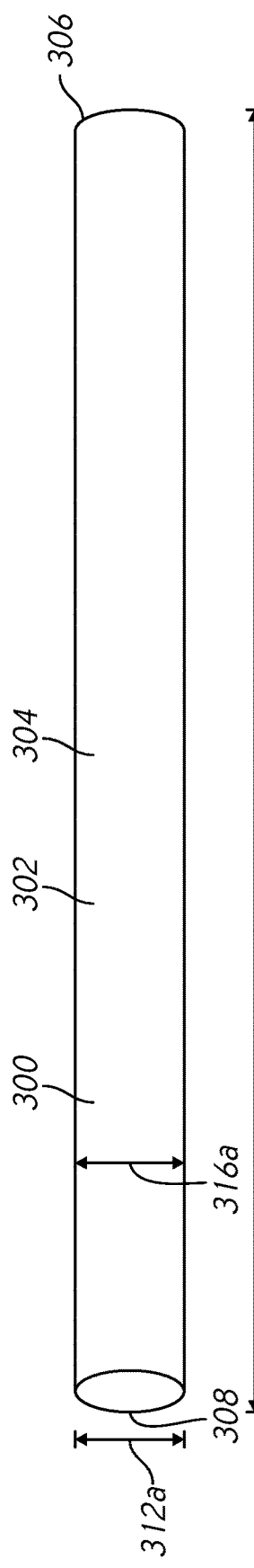
FIGS. 3A and 3B are side perspective views of a stent in accordance with some embodiments.
Figure 3B:
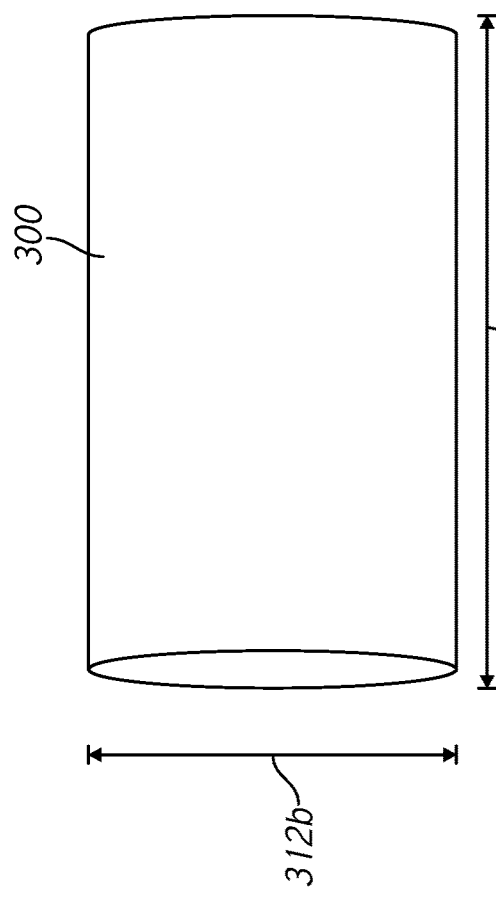

Stents may be self-expanding and may have a primary set configuration, and may also have a secondary set configuration. FIG. 3A depicts a stent 300 in a secondary set configuration, where the stent 300 is a substantially cylindrical main body 302 defined by a stent wall 304, where the stent wall 304 can be porous, such as being formed from a mesh and/or with openings which permit the passage of liquid therethrough. The stent 300 may be open at its distal end 306 and/or at its proximal end 308. The stent 300 has a secondary set outer diameter 312a, a secondary set inner diameter 316a, and a secondary set length 314a. Similarly, FIG. 3B depicts the stent in a primary set configuration, where the stent 300 may be substantially cylindrical and has a primary outer diameter 312b and a primary set length 314b. The primary set outer diameter 312b is larger than the secondary set outer diameter 312a. In the particular example depicted in FIGS. 3A-3B, the stent 300 reduces in length as it radially expands, with the primary set length 314b being shorter than the secondary set length 314a. Depending on the particular design and construction of the stent 300, the stent 300 may lengthen, shorten, or remain the same in length between the primary and secondary set configurations.

Figure 4A:
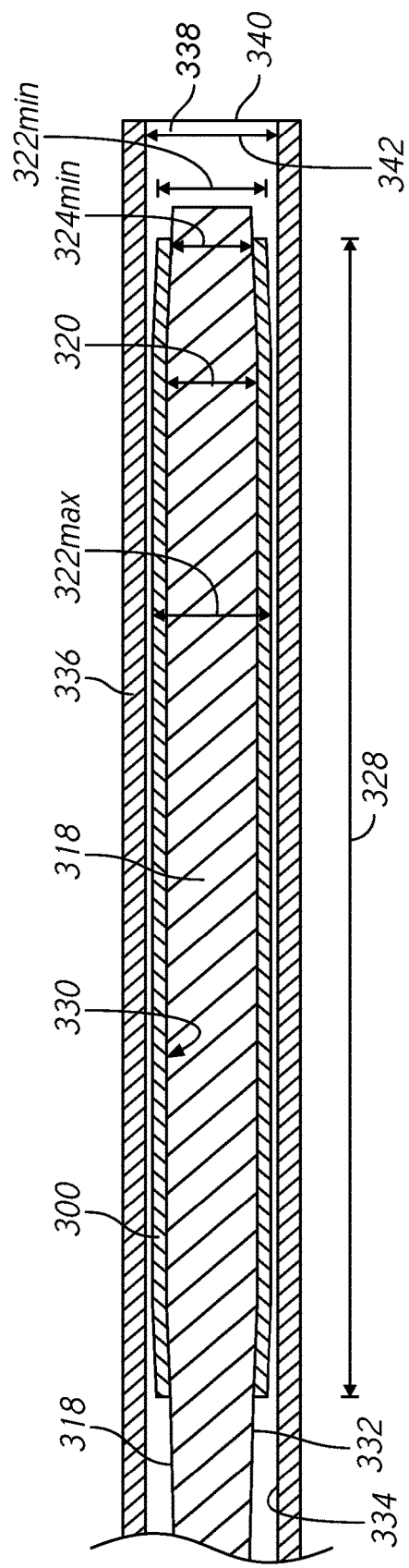
FIGS. 4A and 4B are side cross-sectional views of the stent of FIGS. 3A and 3B.

FIG. 4A depicts the stent 300 of FIGS. 3A-3B in a delivery configuration, wherein the stent 300 is positioned tightly on a core member 318. The portion of the core member 318 on which the stent 300 is positioned may have a core member outer diameter 320 which is at least as large as, and can be slightly larger than, the secondary set inner diameter 316a (depicted in FIG. 3A) of the stent 300, thereby causing the stent 300 when mounted on the core member 318 to be biased radially inwardly against the core member 318 (including any expandable member thereon which may underlie portion(s) of the stent). The stent 300 thus mounted on the core member 318 has a minimum outer delivery diameter 322min, a maximum outer delivery diameter 322max, a minimum inner delivery diameter 324min, and a delivery length 328. Both the minimum and maximum outer delivery diameters 322min, 322max can be the same or larger than the secondary set outer diameter 312a from FIG. 3A, and may be small enough so that the inner surface 330 of the stent 300 engages closely to the outer surface 332 of the core member 318, including the outer surface of an expandable member that may be thereon (not shown). Note that the minimum and maximum outer delivery diameters 322min, 322max can be sufficiently small that the stent 300 during delivery is biased more strongly toward the secondary set configuration and secondary outer diameter 312a of FIG. 3A than to the primary set configuration and primary outer diameter 312b of FIG. 3A. The stent 300 is thus radially exerting an inward force against, and thus held tightly against, the core member 318, and does not exert a radially expansive force against an inner wall 334 of the surrounding catheter 336. Friction between the catheter wall 334/surrounding catheter 336 and the stent 300 is thus reduced, which reduces the pushing and pulling forces needed to advance or withdraw the stent 300 and core member 318 within the catheter lumen 338 and/or out of the catheter distal opening 340. The minimum delivery outer diameter 322min and maximum delivery outer diameter 322max may be equal to or smaller than the inner diameter 342 of the catheter 336.

Note that the various stent diameters and lengths can be selected according to the particular system and application, including the dimensions and shape of the particular lumen where the stent is to be deployed, the inner diameter of any surrounding catheter, the outer diameter of a core member, the diameter and/or length of an expandable member, etc.

Figure 4B:
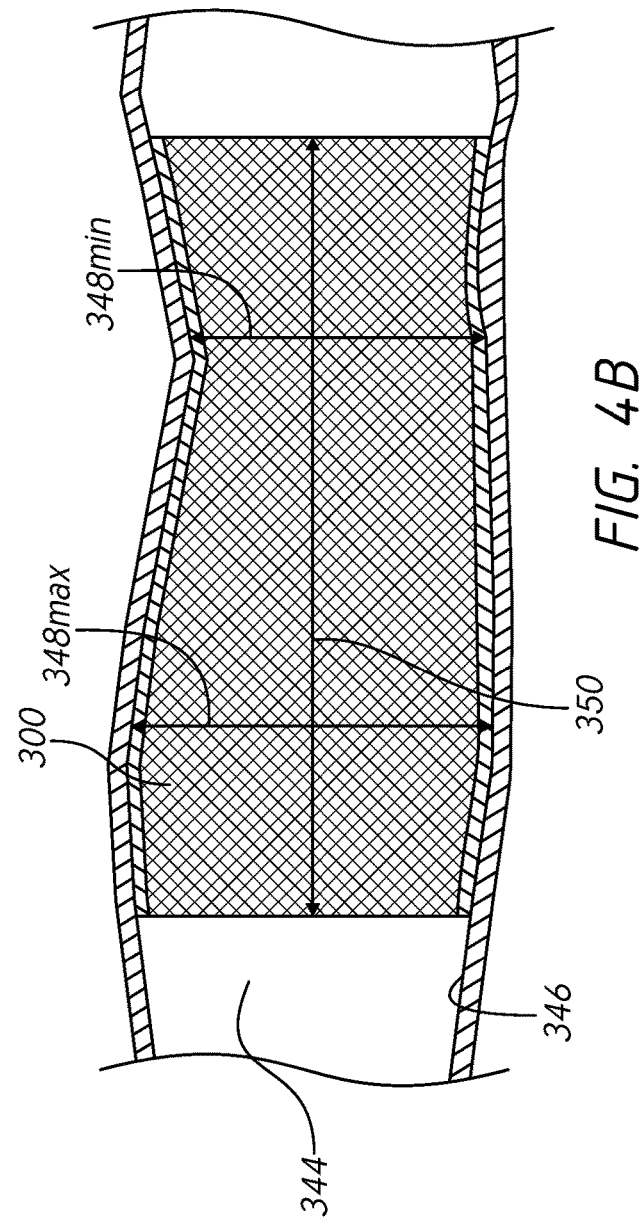
Figure 5:
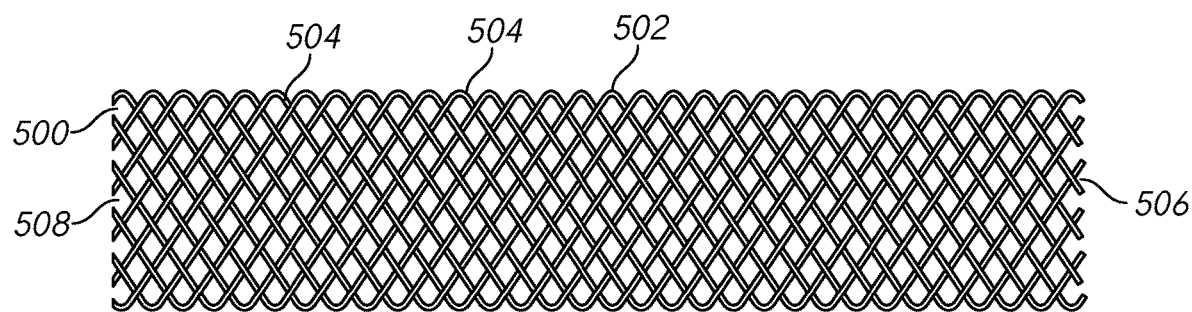
FIG. 5 is a side view of a stent in accordance with some embodiments.

FIG. 4B depicts the stent 300 of FIGS. 3A-3B and 4A in a deployed configuration in a body lumen 344, wherein the stent 300 is released and radially expanded and the catheter and core member have been removed. Radial expansion of the stent 300 may be accomplished in part using radial expansion of an expandable member (not shown) on the core member. The stent 300 is radially expanded into contact with the wall 346 of the body lumen 344. The stent 300 has a minimum deployed diameter 348min, a maximum deployed diameter 348max, and a deployed length 350 (with the length 350 measured along a longitudinal axis of the stent 300, which may be curved to comport to curves in the body lumen 344).

Both the minimum and maximum deployed dimensions 348, 350 are the same or smaller than the primary set diameter 312b of FIG. 3A, but the deployed dimensions 348, 350 may be sufficiently large that the deployed stent 300 is biased more strongly toward the primary set diameter 312b of FIG. 3B than to the secondary set diameter 312a of FIG. 3A. This bias toward the primary set diameter 312b keeps the stent 300 radially expanded against the wall 346 of the body lumen 344, and prevents the stent 300 from collapsing toward the secondary set diameter 312a. Note that if even a small portion of the stent 300 has been expanded toward or at the primary set diameter 312b, with the rest of the stent 300 still contracted close to or at the secondary set outer diameter 312a, the small portion of the stent 300 which is already expanded toward or at the primary set diameter 312b may pull outwardly on the remaining (contracted) portion(s) of the stent 300 with sufficient force to cause the entirety of the stent 300 to expand outwardly toward the primary set outer diameter 312b. This bias prevents undesired narrow portions (e.g., bottlenecks) along the stent 300 when deployed, with the radially expanded portions pulling radially outwardly on any adjacent contracted sections to pull them into radially expanded configuration.

Figure 6:
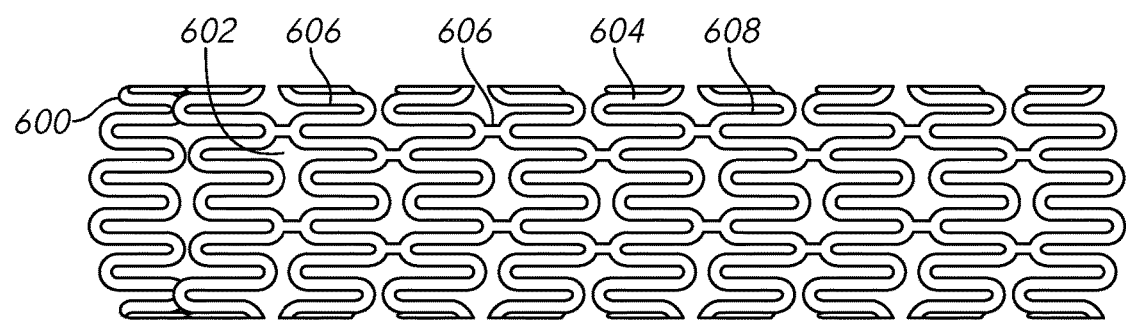
FIG. 6 is a side view of a stent in accordance with some embodiments.
Figure 7:
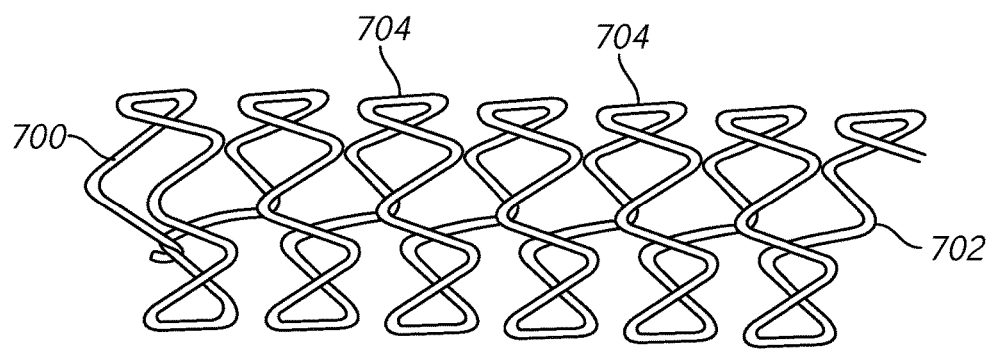
FIG. 7 is a side view of a stent in accordance with some embodiments.

Various stent designs may be used. Examples include a braided stent 500, such as that depicted in FIG. 5. The stent 500 has a central portion 502 formed from braided strand (e.g., wire-like) elements 504, with the braided elements 504 extending from the stent distal end 506 to the stent proximal end 508. FIG. 6 depicts a stent 600 formed by cutting a desired pattern into a hypotube, with cutout areas 602 which are cut (e.g., using a laser) out of a cylindrical body 604, with the remaining (non-cutout) portions 606 defining the lattice wall 608 of the stent 600. A stent 700 may be formed from wire 702, which in the particular example of FIG. 7 is formed into a series of sinusoidal coils 704 defining the length of the stent 700. Note that other types of stents may also be used.

Stents may be formed from various materials, including metals (nitinol, stainless steel, cobalt-chromium, etc.), polymers (e.g., shape-memory thermoplastic and thermoset (covalently cross-linked) polymeric materials), bioresorbable materials, and other materials. Setting the primary and secondary stent configurations may be accomplished by forming the stent using memory materials (such as nitinol), which can be heat-set to one or more specific shapes. Set shapes may also be accomplished by using other stent manufacturing and design methods.

Figure 8A:
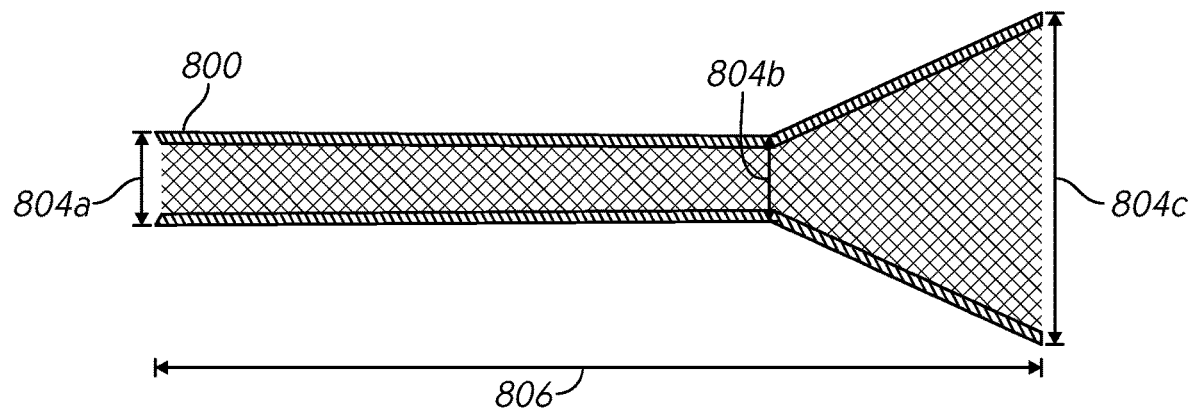
FIGS. 8A and 8B are side cross-sectional views of a stent in accordance with some embodiments.
Figure 8B:
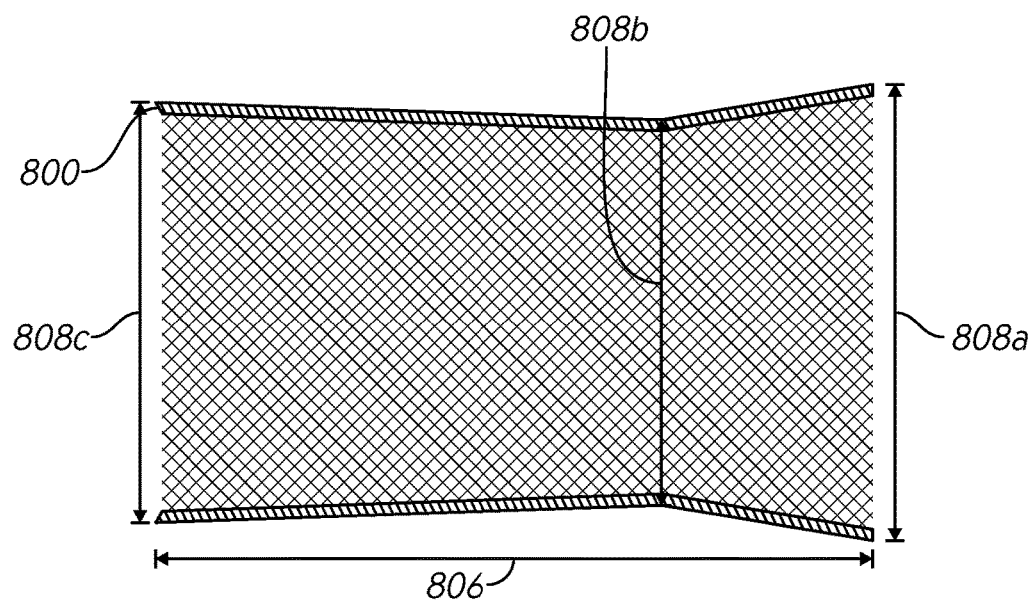

A stent may have one or more set shapes (primary and/or secondary) which have different diameters or other variations in dimensions along the length and/or width/diameter of the stent, including symmetrical and non-symmetrical shapes. As depicted in FIG. 8A, a stent 800 in its secondary set shape has a length 806 with different secondary set outer diameters 804a, 804b, 804c along its length. The secondary set outer diameter 804c at the distal end of the stent is relatively large compared to the smaller secondary set outer diameter 804c at the proximal end the distal end and the even smaller secondary set outer diameter 804b in a section proximal of the distal end of the stent 800. As depicted in FIG. 8B, the stent 800 in its primary set shape has primary set outer diameters 808a (distal), 808b (proximal of distal), 808c (proximal) along its length.

Additional Examples of Expandable Members

In various embodiments, the expandable members can take different forms. For example, the length of the expandable member, the varying diameters of the expandable member, the position of the expandable member on the core member, the shape(s) of the expandable member, the mechanism by which the expandable member is expanded and/or contracted, the control of the expandable member, the material selected, and dimensions can all vary to achieve desired operation of the expandable member. FIGS. 9-11B illustrate various alternative embodiments of expandable members. These expandable members can be incorporated into and combined with the systems and core members and stents described above with respect to FIGS. 1A-8B. Additionally, aspects of these expandable members can be combined and intermixed such that features of any one of these expandable members (e.g., the diameters, configuration, mechanism of expansion, etc.) can be combined with the features of any of the other delivery systems and/or stents disclosed herein (e.g., the type of stent, type of delivery system (such as core member), etc.

An expandable member may have a compressed/delivery diameter not significantly greater than the diameters of surrounding portions of the core member. The expandable member may have an expanded diameter which is sufficient to radially expand the overlying portion of the stent to a diameter which is sufficiently large so that that portion of the stent when expanded by the expandable member is biased toward the primary (expanded) set configuration and not toward the secondary (smaller) set configuration. In various embodiments, expandable members can have various lengths, diameters (expanded and contracted), shapes, designs, etc., depending on the particular application and parameters such as the deployment site, stent size/diameters/length, etc.

Figure 9:
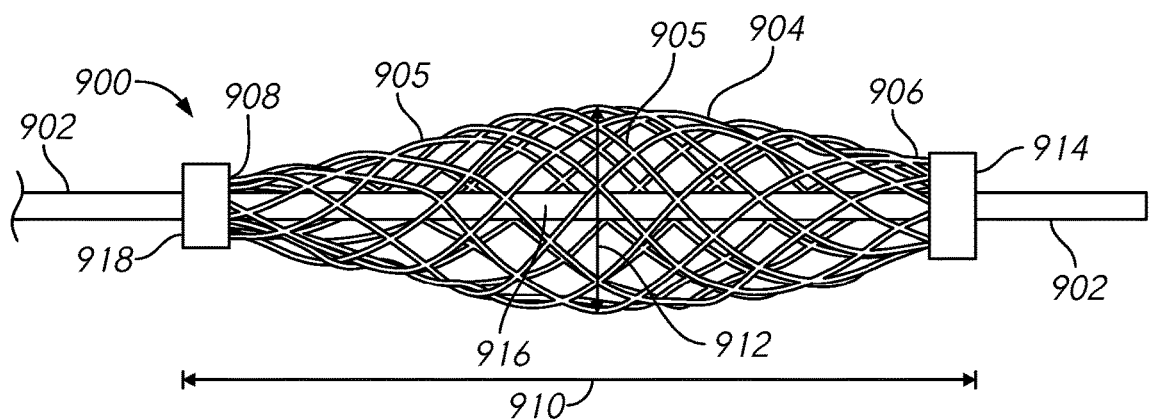
FIG. 9 is a side view of an expandable member in accordance with some embodiments.

FIG. 9 illustrates, in partially expanded configuration, another embodiment of an expandable member 900 positioned on a core member 902. The expandable member 900 has a braided main body 904 formed from braided elements 905 and having a distal end 906 and a proximal end 908, and a length 910 and maximum diameter 912. The braided main body 904 is secured at its distal end 906 to a distal collar 914 mounted around the core member central body 916, and the proximal end 908 is secured to a proximal collar 918 mounted around the core member central body 916. At least one of the distal collar 914 and the proximal collar 918 are slidingly secured around the core member central body 916, so that one of the collars 914, 918 can be advanced toward the other collar and can also be moved away from the other collar. Movement of one of the collars 914, 918 toward the other collar causes radial expansion/increased diameter 912 (and reduced length 910) of the expandable member 900. Movement of one of the collars 914, 918 away from the other collar causes radial contraction/reduced diameter 912 (and increased length 910) of the braided main body 904. Selective radial expansion of the expandable member 900 can facilitate expansion and deployment of a stent (not shown), as discussed elsewhere in this application. Additionally or alternatively, the expandable member 900 can be self-expanding such that it is biased towards a radially expanded configuration, while being collapsible to the reduced-diameter configuration for delivery. In various embodiments, one or both of the collars 914 and 918 can be fixed or slidably coupled to the underlying core member 902 depending on the desired configuration.

Figure 10A:
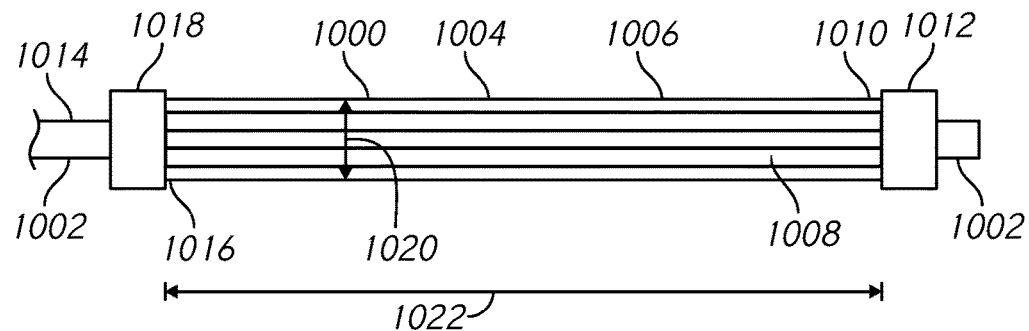
FIGS. 10A and 10B are side views of an expandable member in accordance with some embodiments.
Figure 10B:
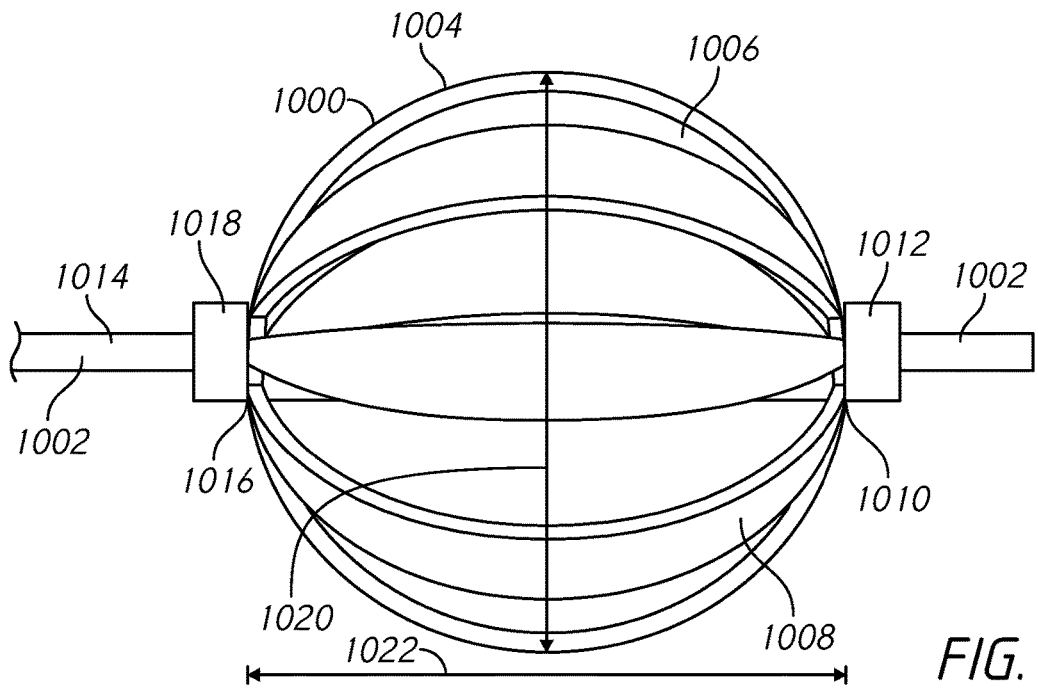

FIGS. 10A and 10B illustrate, in compressed and expanded configurations, respectively, another embodiment of an expandable member 1000 positioned on a core member 1002. The expandable member 1000 has a main body 1004 which includes openings therethrough. In the example of FIG. 10A, the main body 1004 is a cylindrical form into which openings have been formed, such as by cutting openings therein (e.g., via laser cutting) such as the depicted longitudinal slots 1006 separating longitudinal slats 1008. The expandable member distal end 1010 is secured to a distal collar 1012 mounted around the core member central body 1014, and the expandable member proximal end 1016 is secured to a proximal collar 1018 mounted around the core member central body 1014. At least one of the distal collar 1012 and the proximal collar 1018 are slidingly secured around the core member central body 1014, so that one of the collars 1012, 1018 can be advanced toward the other collar and can also be moved away from the other collar. Movement of one of the collars 1012, 1018 toward the other collar causes the slats 1008 to bend and curve, resulting in radial expansion/increase of the diameter 1020 (and reduced length 1022) of the expandable member 1000, as depicted in FIG. 10B. Movement of one of the collars 1012, 1018 away from the other collar causes radial contraction/reduced diameter 1020 (and increased length 1022) of the expandable member 1000, as depicted in FIG. 10A. Selective radial expansion of the expandable member 1000 can facilitate expansion and deployment of a stent (not shown), as discussed elsewhere in this application. Additionally or alternatively, the expandable member 1000 can be self-expanding such that it is biased towards a radially expanded configuration, while being collapsible toward the compressed configuration to underlie the stent within the catheter. In various embodiments, one or both of the collars 1012 and 1018 can be fixed or slidably coupled to the underlying core member 1002 depending on the desired configuration.

Figure 11A:
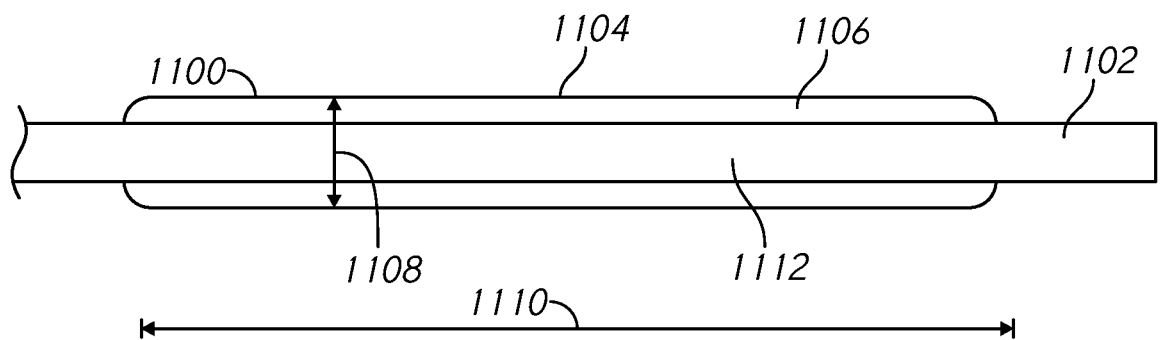
FIGS. 11A and 11B are side cross-sectional views of an expandable member in accordance with some embodiments.
Figure 11B:
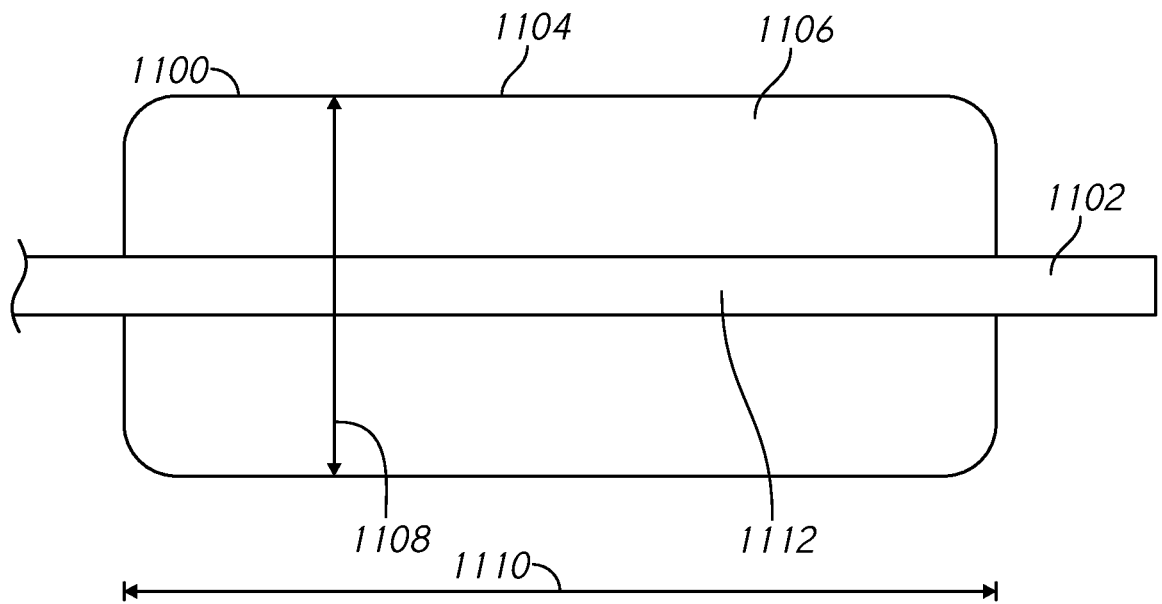

FIGS. 11A and 11B illustrate, in compressed and expanded configurations, respectively, another embodiment of an expandable member 1100 positioned on a core member 1102. The expandable member 1100 has a balloon 1104 which includes an inner reservoir 1106 has an outer diameter 1108 and length 1110. In the example of FIG. 11A, the balloon 1104 is uninflated, with the inner reservoir 1106 substantially or completely empty, so that the balloon 1104 is contracted against the core member inner element 1112. Injection of a gas (e.g., air) and/or liquid (e.g., saline solution) into the balloon inner reservoir 1106, such as via a balloon inflation lumen (not shown), will inflate the balloon 1104 thereby causing radial expansion of the expandable member 1100 to a desired outer diameter 1108, as depicted in FIG. 11B. Subsequent removal of the gas and/or liquid from the inner reservoir 1106 of the balloon 1104 will cause radial contraction/reduction in the diameter 1108 of the expandable member 1100, as depicted in FIG. 11A. Selective radial expansion of the expandable member 1100 can facilitate expansion and deployment of a stent (not shown), as discussed elsewhere in this application.

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

The invention claimed is:

1. A stent delivery system, comprising:
   a core member configured for advancement within a corporeal lumen;
   an expandable member positioned on the core member such that a first end is secured to the core member and a second end is slidingly coupled to the core member, wherein the expandable member is adapted to be radially expanded from a collapsed delivery configuration to an expanded configuration;
   an actuator coupled to the expandable member second end and configured such that movement of the actuator selectively expands the expandable member from the collapsed delivery configuration to the expanded configuration, wherein movement of the actuator in a first direction moves the second end toward the first end, thereby causing the expandable member to shorten and radially expand, and wherein relative movement of the actuator in a second direction moves the second end away from the first end, thereby causing the expandable member to lengthen and radially compress;
   a stent extending along the core member and over the expandable member, the stent having a primary set configuration with a radially expanded state and a secondary set configuration with a radially low-profile state, the stent assuming a stent delivery configuration in which the stent is more strongly biased towards the secondary set configuration such that the stent is radially compressed against the core member until expanded via the expandable member, and wherein the stent is configured such that, after the underlying expandable member expands the stent, the stent is more strongly biased towards the primary set configuration such that the stent continues to expand after the expandable member has finished expanding until the stent assumes a stent expanded configuration in which the stent is radially expanded from the stent delivery configuration, wherein the stent expanded configuration has a greater radial dimension than the expandable member expanded configuration; and
   a proximal coupling assembly disposed over the core member and underlying a proximal portion of the stent, the proximal coupling assembly positioned proximal to the expandable member, wherein the proximal coupling assembly comprises one or more stent engagement members configured to engage an inner wall of the stent against an overlying catheter,
   wherein, in the collapsed delivery configuration, the expandable member underlies the stent along less than half the entire length of the stent.

2. The system of claim 1, wherein the expandable member comprises a main body having a cylindrical shape when the expandable member is in the collapsed delivery configuration.

3. The system of claim 1, wherein, in the expanded configuration, the expandable member contacts the stent along less than half of the entire length of the stent.

4. The system of claim 1, further comprising a catheter through which the core member and stent are configured to be slidably advanced.

5. The system of claim 1, wherein the stent is formed from a shape memory material.

6. The system of claim 1, wherein the stent is heat-set into the primary set configuration.

7. The system of claim 1, wherein the stent is heat-set into the secondary set configuration.

8. The system of claim 1, wherein the proximal coupling assembly is configured to enable resheathing of the stent within the overlying catheter after a distal portion of the stent has been expanded via the expandable member.

9. A stent delivery system, comprising:
   a core member configured for advancement within a corporeal lumen;
   an expandable member coupled to the core member, the expandable member having a first end and a second end;
   an actuator coupled to the expandable member and configured such that (1) movement of the actuator in a first direction causes the first end and second end of the expandable member to be moved closer together, thereby expanding the expandable member, and (2) movement of the actuator in a second direction causes the first end and second end of the expandable member to move further apart, thereby collapsing the expandable member;
   a stent extending along the core member and over the expandable member, the stent comprising a memory material, the stent further comprising a stent delivery configuration wherein the stent is radially compressed against the core member and comprises a maximum stent delivery diameter, wherein the stent is characterized by the memory material having a secondary set configuration wherein the stent is radially compressed and comprises a secondary stent maximum diameter which is no greater than the maximum stent delivery diameter, and wherein the stent is further characterized by the memory material having a primary set configuration wherein the stent is radially expanded and comprises a primary set maximum diameter which is greater than the maximum stent delivery diameter; and
   a proximal coupling assembly disposed over the core member and underlying a proximal portion of the stent, the proximal coupling assembly positioned proximal to the expandable member, wherein the proximal coupling assembly comprises one or more stent engagement members configured to engage an inner wall of the stent against an overlying catheter, wherein, in the stent delivery configuration, the expandable member underlies the stent along less than half the entire length of the stent, and wherein, when the stent is in the stent delivery configuration, the stent is more strongly biased towards the second set configuration, and wherein, after the underlying expandable member expands the stent, the stent is more strongly biased towards the primary set configuration such that the stent continues to expand after the expandable member has finished expanding.

10. The stent delivery system of claim 9, wherein the stent is adapted to be deployed within a body lumen, wherein the stent after deployment in the body lumen comprises a stent expanded configuration wherein the stent is radially expanded against a wall of the body lumen and wherein the stent comprises a maximum stent expanded diameter which is no greater than the primary set maximum diameter.

11. The system of claim 9, wherein the stent is formed from a shape memory material.

12. The system of claim 9, wherein the stent is heat-set into the primary set configuration.

13. The system of claim 9, wherein the stent is heat-set into the secondary set configuration.

14. The system of claim 9, wherein the expandable member is adapted to be selectively radially expanded from a collapsed delivery configuration to an expanded deployment configuration.

15. A stent delivery system, comprising:
a core member configured for advancement within a corporeal lumen;
an expandable member coupled to the core member, the expandable member having a first end and a second end; an actuator coupled to the expandable member and configured such that (1) movement of the actuator in a first direction causes the first end and second end of the expandable member to be moved closer together, thereby expanding the expandable member, and (2) movement of the actuator in a second direction causes the first end and second end of the expandable member to move further apart, thereby collapsing the expandable member; and
a stent extending along the core member and over the expandable member, the stent comprising a memory material having a primary set configuration in which the stent is radially expanded and a secondary set configuration in which the stent is radially collapsed, wherein the stent is configured to maintain the secondary set configuration until the expandable member expands against the stent to urge the stent radially outwardly to a first expanded state, and wherein the stent is configured to continue expanding after the expandable member has finished expanding such that the stent assumes a second, larger expanded state, wherein in the secondary set configuration, the expandable member underlies the stent along less than half the entire length of the stent; and
a proximal coupling assembly disposed over the core member and underlying a proximal portion of the stent, the proximal coupling assembly positioned proximal to the expandable member, wherein the proximal coupling assembly comprises one or more stent engagement members configured to engage an inner wall of the stent against an overlying catheter.

16. The stent delivery system of claim 15, wherein in the secondary set configuration, the stent is biased towards a collapsed configuration in which a radially outermost dimension of the stent is less than a radially outermost dimension of the core member.

17. The stent delivery system of claim 15, wherein in the primary set configuration, the stent is biased towards an expanded configuration in which a radially outermost dimension of the stent is greater than an outermost dimension of the expandable member in an expanded state.

18. The stent delivery system of claim 15, wherein the actuator comprises a pull wire.

19. The stent delivery system of claim 15, wherein the expandable member comprises at least one of: a braid, a mesh, a slotted hypotube, or a coil.

* * * * *